(12) United States Patent
Latz et al.

(10) Patent No.: US 9,409,968 B2
(45) Date of Patent: Aug. 9, 2016

(54) TOLL-LIKE RECEPTOR-BASED BIOSENSORS

(75) Inventors: Eicke Latz, Bonn (DE); Gabor Horvath, Bonn (DE)

(73) Assignee: University of Massachusetts, Boston, MA (US)

( * ) Notice: Subject to any disclaimer, the term of this patent is extended or adjusted under 35 U.S.C. 154(b) by 471 days.

(21) Appl. No.: 13/265,250

(22) PCT Filed: Apr. 23, 2010

(86) PCT No.: PCT/US2010/032265
§ 371 (c)(1),
(2), (4) Date: Nov. 18, 2011

(87) PCT Pub. No.: WO2010/124226
PCT Pub. Date: Oct. 28, 2010

(65) Prior Publication Data
US 2012/0053081 A1    Mar. 1, 2012

Related U.S. Application Data

(60) Provisional application No. 61/214,423, filed on Apr. 23, 2009.

(51) Int. Cl.
| | | |
|---|---|---|
| G01N 33/53 | (2006.01) | |
| C07K 14/705 | (2006.01) | |
| G01N 33/566 | (2006.01) | |
| G01N 33/569 | (2006.01) | |
| C07K 14/00 | (2006.01) | |

(52) U.S. Cl.
CPC ............ *C07K 14/705* (2013.01); *G01N 33/566* (2013.01); *G01N 33/56911* (2013.01)

(58) Field of Classification Search
None
See application file for complete search history.

(56) References Cited

PUBLICATIONS

Akira et al., "Pathogen Recognition and Innate Immunity," *Cell.*, vol. 124, pp. 783-801, Jan. 24, 2006.
International Search Report and Written Opinion; PCT/US2010/032265; mailed Jan. 14, 2011.
Janssens and Beyaert, "Role of Toll-Like Receptors in Pathogen Recognition," *Clinical Microbiology Reviews*, vol. 16, No. 4, pp. 637-646, Aug. 31, 2003.
Kanzler et al., "Therapeutic Targeting of Innate Immunity with Toll-Like Receptor Agonists and Antagonists," *Nature Medicine*, vol. 13, No. 5, pp. 552-559, May 3, 2007.
Kawai and Akira, "Pathogen Recognition with Toll-Like Receptors," *Current Opinion in Immunology*, vol. 17, pp. 338-344, Jun. 13, 2005.
Jessica K. Bell et al., "Leucine-rich repeats and pathogen recognition in Toll-like receptors", Opinion—Trends in Immunology 24:528-533, 2003.
Adrian Ozinsky et al., "The repertoire for pattern recognition of pathogens by the innate immune system is defined by cooperation between Toll-like receptors", Proc Natl Acad Sci USA 97:13766-13771, 2000.

*Primary Examiner* — Nancy T Vogel
(74) *Attorney, Agent, or Firm* — Fish & Richardson P.C.

(57) ABSTRACT

Compositions and methods for detecting Toll-like receptor binding to ligands and test compounds are disclosed herein.

18 Claims, 13 Drawing Sheets

FRET measurement calculation

$$I_1(\text{excD emD}) = I_D(1-E) + I_A S_4 + \frac{S_4}{S_2} \cdot I_D E$$

$$I_2(\text{excD emA}) = I_D(1-E)S_1 + I_A S_2 + I_D E$$

$$I_3(\text{excA emA}) = I_D(1-E)S_3 + I_A + \frac{S_3}{S_1} \cdot I_D E$$

$$A = \frac{E}{1-E} = \frac{1}{a} \times \frac{S_1 S_2 \left[ I_2(1-S_3 S_4) - I_1(S_1 - S_2 S_3) - I_3(S_2 - S_1 S_4) \right]}{(S_1 - S_2 S_3)(I_1 S_2 - I_2 S_4)}$$

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: laboratory-synthesized primer

<400> SEQUENCE: 1
tgctcctgga ggggttgt                                                    18

<210> SEQ ID NO 2
<211> LENGTH: 1032
<212> TYPE: PRT
<213> ORGANISM: Homo sapien

<400> SEQUENCE: 2

Met Gly Phe Cys Arg Ser Ala Leu His Pro Leu Ser Leu Leu Val Gln
 1               5                  10                  15
```

```
Ala Ile Met Leu Ala Met Thr Leu Ala Leu Gly Thr Leu Pro Ala Phe
            20                  25                  30

Leu Pro Cys Glu Leu Gln Pro His Gly Leu Val Asn Cys Asn Trp Leu
        35                  40                  45

Phe Leu Lys Ser Val Pro His Phe Ser Met Ala Ala Pro Arg Gly Asn
    50                  55                  60

Val Thr Ser Leu Ser Leu Ser Ser Asn Arg Ile His His Leu His Asp
65                  70                  75                  80

Ser Asp Phe Ala His Leu Pro Ser Leu Arg His Leu Asn Leu Lys Trp
                85                  90                  95

Asn Cys Pro Pro Val Gly Leu Ser Pro Met His Phe Pro Cys His Met
            100                 105                 110

Thr Ile Glu Pro Ser Thr Phe Leu Ala Val Pro Thr Leu Glu Glu Leu
        115                 120                 125

Asn Leu Ser Tyr Asn Asn Ile Met Thr Val Pro Ala Leu Pro Lys Ser
    130                 135                 140

Leu Ile Ser Leu Ser Leu Ser His Thr Asn Ile Leu Met Leu Asp Ser
145                 150                 155                 160

Ala Ser Leu Ala Gly Leu His Ala Ile Arg Phe Leu Phe Met Asp Gly
                165                 170                 175

Asn Cys Tyr Tyr Lys Asn Pro Cys Arg Gln Ala Leu Glu Val Ala Pro
            180                 185                 190

Gly Ala Leu Leu Gly Leu Gly Asn Leu Thr His Leu Ser Leu Lys Tyr
        195                 200                 205

Asn Asn Leu Thr Val Val Pro Arg Asn Leu Pro Ser Ser Leu Glu Tyr
    210                 215                 220

Leu Leu Leu Ser Tyr Asn Arg Ile Val Lys Leu Ala Pro Glu Asp Leu
225                 230                 235                 240

Ala Asn Leu Thr Ala Leu Arg Val Leu Asp Val Gly Gly Asn Cys Arg
                245                 250                 255

Arg Cys Asp His Ala Pro Asn Pro Cys Met Glu Cys Pro Arg His Phe
            260                 265                 270

Pro Gln Leu His Pro Asp Thr Phe Ser His Leu Ser Arg Leu Glu Gly
        275                 280                 285

Leu Val Leu Lys Asp Ser Ser Leu Ser Trp Leu Asn Ala Ser Trp Phe
    290                 295                 300

Arg Gly Leu Gly Asn Leu Arg Val Leu Asp Leu Ser Glu Asn Phe Leu
305                 310                 315                 320

Tyr Lys Cys Ile Thr Lys Thr Lys Ala Phe Gln Gly Leu Thr Gln Leu
                325                 330                 335

Arg Lys Leu Asn Leu Ser Phe Asn Tyr Gln Lys Arg Val Ser Phe Ala
            340                 345                 350

His Leu Ser Leu Ala Pro Ser Phe Gly Ser Leu Val Ala Leu Lys Glu
        355                 360                 365

Leu Asp Met His Gly Ile Phe Phe Arg Ser Leu Asp Glu Thr Thr Leu
    370                 375                 380

Arg Pro Leu Ala Arg Leu Pro Met Leu Gln Thr Leu Arg Leu Gln Met
385                 390                 395                 400

Asn Phe Ile Asn Gln Ala Gln Leu Gly Ile Phe Arg Ala Phe Pro Gly
                405                 410                 415

Leu Arg Tyr Val Asp Leu Ser Asp Asn Arg Ile Ser Gly Ala Ser Glu
            420                 425                 430
```

-continued

```
Leu Thr Ala Thr Met Gly Glu Ala Asp Gly Gly Glu Lys Val Trp Leu
            435                 440                 445

Gln Pro Gly Asp Leu Ala Pro Ala Pro Val Asp Thr Pro Ser Ser Glu
            450                 455                 460

Asp Phe Arg Pro Asn Cys Ser Thr Leu Asn Phe Thr Leu Asp Leu Ser
465                 470                 475                 480

Arg Asn Asn Leu Val Thr Val Gln Pro Glu Met Phe Ala Gln Leu Ser
                485                 490                 495

His Leu Gln Cys Leu Arg Leu Ser His Asn Cys Ile Ser Gln Ala Val
            500                 505                 510

Asn Gly Ser Gln Phe Leu Pro Leu Thr Gly Leu Gln Val Leu Asp Leu
            515                 520                 525

Ser His Asn Lys Leu Asp Leu Tyr His Glu His Ser Phe Thr Glu Leu
530                 535                 540

Pro Arg Leu Glu Ala Leu Asp Leu Ser Tyr Asn Ser Gln Pro Phe Gly
545                 550                 555                 560

Met Gln Gly Val Gly His Asn Phe Ser Phe Val Ala His Leu Arg Thr
                565                 570                 575

Leu Arg His Leu Ser Leu Ala His Asn Asn Ile His Ser Gln Val Ser
            580                 585                 590

Gln Gln Leu Cys Ser Thr Ser Leu Arg Ala Leu Asp Phe Ser Gly Asn
            595                 600                 605

Ala Leu Gly His Met Trp Ala Glu Gly Asp Leu Tyr Leu His Phe Phe
            610                 615                 620

Gln Gly Leu Ser Gly Leu Ile Trp Leu Asp Leu Ser Gln Asn Arg Leu
625                 630                 635                 640

His Thr Leu Leu Pro Gln Thr Leu Arg Asn Leu Pro Lys Ser Leu Gln
                645                 650                 655

Val Leu Arg Leu Arg Asp Asn Tyr Leu Ala Phe Phe Lys Trp Trp Ser
            660                 665                 670

Leu His Phe Leu Pro Lys Leu Glu Val Leu Asp Leu Ala Gly Asn Gln
            675                 680                 685

Leu Lys Ala Leu Thr Asn Gly Ser Leu Pro Ala Gly Thr Arg Leu Arg
            690                 695                 700

Arg Leu Asp Val Ser Cys Asn Ser Ile Ser Phe Val Ala Pro Gly Phe
705                 710                 715                 720

Phe Ser Lys Ala Lys Glu Leu Arg Glu Leu Asn Leu Ser Ala Asn Ala
                725                 730                 735

Leu Lys Thr Val Asp His Ser Trp Phe Gly Pro Leu Ala Ser Ala Leu
            740                 745                 750

Gln Ile Leu Asp Val Ser Ala Asn Pro Leu His Cys Ala Cys Gly Ala
            755                 760                 765

Ala Phe Met Asp Phe Leu Leu Glu Val Gln Ala Ala Val Pro Gly Leu
            770                 775                 780

Pro Ser Arg Val Lys Cys Gly Ser Pro Gly Gln Leu Gln Gly Leu Ser
785                 790                 795                 800

Ile Phe Ala Gln Asp Leu Arg Leu Cys Leu Asp Glu Ala Leu Ser Trp
                805                 810                 815

Asp Cys Phe Ala Leu Ser Leu Leu Ala Val Ala Leu Gly Leu Gly Val
            820                 825                 830

Pro Met Leu His His Leu Cys Gly Trp Asp Leu Trp Tyr Cys Phe His
            835                 840                 845

Leu Cys Leu Ala Trp Leu Pro Trp Arg Gly Arg Gln Ser Gly Arg Asp
```

```
                  850                 855                 860

Glu Asp Ala Leu Pro Tyr Asp Ala Phe Val Val Phe Asp Lys Thr Gln
865                 870                 875                 880

Ser Ala Val Ala Asp Trp Val Tyr Asn Glu Leu Arg Gly Gln Leu Glu
                885                 890                 895

Glu Cys Arg Gly Arg Trp Ala Leu Arg Leu Cys Leu Glu Glu Arg Asp
                900                 905                 910

Trp Leu Pro Gly Lys Thr Leu Phe Glu Asn Leu Trp Ala Ser Val Tyr
                915                 920                 925

Gly Ser Arg Lys Thr Leu Phe Val Leu Ala His Thr Asp Arg Val Ser
    930                 935                 940

Gly Leu Leu Arg Ala Ser Phe Leu Leu Ala Gln Gln Arg Leu Leu Glu
945                 950                 955                 960

Asp Arg Lys Asp Val Val Leu Val Ile Leu Ser Pro Asp Gly Arg
                965                 970                 975

Arg Ser Arg Tyr Val Arg Leu Arg Gln Arg Leu Cys Arg Gln Ser Val
                980                 985                 990

Leu Leu Trp Pro His Gln Pro Ser Gly Gln Arg Ser Phe Trp Ala Gln
                995                 1000                1005

Leu Gly Met Ala Leu Thr Arg Asp Asn His His Phe Tyr Asn Arg Asn
    1010                1015                1020

Phe Cys Gln Gly Pro Thr Ala Glu
1025                1030

<210> SEQ ID NO 3
<211> LENGTH: 36
<212> TYPE: DNA
<213> ORGANISM: Artificial Sequence
<220> FEATURE:
<223> OTHER INFORMATION: laboratory-sythesized primer

<400> SEQUENCE: 3
ctgaacgaat tcgccgctag catggtgagc aagggc                           36

<210> SEQ ID NO 4
<211> LENGTH: 36
<212> TYPE: DNA
<213> ORGANISM: Artificial Sequence
<220> FEATURE:
<223> OTHER INFORMATION: laboratory-sythesized primer

<400> SEQUENCE: 4
ggatatctag actcgagtta cttgtacagc tcgtcc                           36

<210> SEQ ID NO 5
<211> LENGTH: 32
<212> TYPE: DNA
<213> ORGANISM: Artificial Sequence
<220> FEATURE:
<223> OTHER INFORMATION: laboratory-sythesized primer

<400> SEQUENCE: 5
gacccggatc cgcggccgcc accatgggct gc                               32

<210> SEQ ID NO 6
<211> LENGTH: 40
<212> TYPE: DNA
<213> ORGANISM: Artificial Sequence
<220> FEATURE:
<223> OTHER INFORMATION: laboratory-sythesized primer
```

```
<400> SEQUENCE: 6
gatgggaatt cggcatcgat tgccttgtac agctcgtcca                        40
```

TOLL-LIKE RECEPTOR-BASED BIOSENSORS

CROSS-REFERENCE TO RELATED APPLICATIONS

This application is a U.S. national stage application under 35 U.S.C. §371 of International Application Number PCT/US2010/032265, filed on Apr. 23, 2010, which claims priority under 35 U.S.C. §119 to U.S. provisional patent application No. 61/214,423, filed Apr. 23, 2009, the contents of which are hereby incorporated by reference in their entirety.

TECHNICAL FIELD

Compositions and methods disclosed herein relate to methods of detecting Toll-like receptor binding to ligands and test compounds.

BACKGROUND

In multicellular organisms, about 5% of the genome is devoted to proteins acting in the defense against infections (Lander, E. S. et al., Nature 409, 860-921, 2001; Waterston, R. H. et al., Nature 420, 520-562, 2002, each of which is incorporated by reference in its entirety). Loss or dysfunction of certain defense genes results in increased vulnerability to infection as exemplified by over 80 known primary human immunodeficiencies (Waterston, R. H. et al., Nature 420, 520-562, 2002, incorporated by reference in its entirety). Immune cells respond to the presence of microbes with an increased capacity to destroy the invading pathogen concomitant with the production of a variety of potent cytokines and other inflammatory mediators. The produced inflammatory molecules have the capacity to activate many more immune cells and other effector cells distant to the focus of the infectious site, which can lead to a coordinated immune response to the infectious agents.

Toll-like receptor (TLRs) TLRs are transmembrane signaling receptors that can directly bind to a wide spectrum of microbial structures that include lipids. After ligand binding, signaling pathways can be activated leading to transcription of genes involved in the defense against the invading microbes. The importance of TLRs in the detection of microbial pathogens and their role in the induction of mechanisms intended to clear the infection is now well-documented (Hemmi, H. et al., Nature 408, 740-745, 2000; Takeuchi, O., Hoshino, K. & Akira, S., J Immunol 165, 5392-5396, 2000; Takeuchi, O. et al., Immunity 11, 443-451, 1999, each of which is incorporated by reference in its entirety). Certain members of the TLR family are also involved in the recognition of self-epitopes that appear in non-infectious alterations of the normal physiological state.

SUMMARY

Compositions and methods disclosed herein relate to methods of detecting Toll-like receptor binding to ligands and test compounds.

In certain embodiments, the present disclosure provides methods for diagnosing a gram negative or gram positive infection in a subject, comprising providing a plurality of biosensor complexes, each biosensor complex comprising a toll-like receptor (TLR) ligand binding domain conjugated to a solid support, providing a sample from a subject, contacting the sample to the plurality of biosensor complexes, and detecting binding of the TLR ligand binding domains to their cognate ligands in the presence and absence of the sample. In certain embodiments, at least one biosensor complex of the plurality comprises a TLR2 ligand binding domain. In certain embodiments, at least one biosensor complex of the plurality comprises a TLR4 ligand binding domain. In certain embodiments, a decrease in binding of the TLR2 to its cognate ligand in the presence of the sample indicates that the subject has an infection with a gram positive bacterium, and a decrease in binding of the TLR4 to its cognate ligand in the presence of the sample indicates that the subject has an infection with a gram negative bacterium. In certain embodiments, the plurality of biosensor complexes further comprises at least one biosensor complex comprising a TLR9 ligand binding domain bound to its cognate ligand, and wherein a decrease in binding of the TLR9 ligand binding domain to its cognate ligand indicates the presence of a lysed bacterium in the sample. In certain embodiments, the plurality of biosensor complexes further comprises at least one biosensor complex comprising a TLR9 ligand binding domain bound to its cognate ligand, and wherein a decrease in binding of the TLR9 ligand binding domain to its cognate ligand indicates the presence of a lysed bacterium in the sample and at least one cognate ligand is fluorescently labeled, the fluorescence emission spectrum of the fluorescently labeled solid support overlaps with the absorption spectrum of the fluorescently labeled cognate ligand, and a decrease in binding is detected by detecting a change in fluorescence emissions from the biosensor complex.

In certain embodiments, the present disclosure provides methods for selecting a treatment for a subject having an inflammatory condition, comprising providing a plurality of biosensor complexes, each biosensor complex comprising a toll-like receptor (TLR) ligand binding domain conjugated to a solid support, wherein at least one TLR ligand binding domain is different from the other TLR binding domains of the biosensor complexes, wherein each biosensor complex further comprises a cognate ligand bound to the TLR ligand binding domain, providing a sample comprising a biological fluid or tissue from the subject, contacting the sample to the plurality of biosensor complexes, and detecting a change in binding of at least one TLR to its cognate ligand binding domain, wherein a change in binding indicates the presence of a ligand for the TLR ligand binding domain in the sample, identifying which biosensor complex or complexes bind ligands present in the sample, and selecting a treatment for the subject based on the identity of the TLR ligand binding domain bound by the ligand in the sample. In certain embodiments, the treatment comprises administration of a therapeutic agent to the subject, wherein the therapeutic agent specifically inhibits the TLR bound by the ligand in the sample. In certain embodiments, at least one of the TLRs is TLR4, and the therapeutic agent comprises TAK-242. In certain embodiments, at least one of the TLRs is TLR4, and the therapeutic agent comprises eritoran. In certain embodiments, at least one of the TLRs is TLR2, and the therapeutic agent comprises the humanized antibody OPN-305. In certain embodiments, at least one of the TLRs is TLR7 or TLR9, and the therapeutic agent comprises a nucleic acid molecule shown in SEQ ID NO: 1. In certain embodiments, at least one of the TLRs is TLR7 or TLR9, and the therapeutic agent comprises IMO-3100. In certain embodiments, at least one of the TLRs is TLR7, TLR8, or TLR9, and the therapeutic agent comprises CPG 52364.

In certain embodiments, the subject is a human. In certain embodiments, the sample comprises a material obtained from a subject, the material selected from the group consisting of: amniotic fluid, blood, blood cells, cerebrospinal fluid, fine needle biopsy samples, peritoneal fluid, plasma, pleural fluid, saliva, semen, serum, sputum, tissue or tissue homogenates, tissue culture media, and urine. In certain embodiments, the sample comprises material obtained from a fluid or tissue associated with or affected by the inflammatory condition.

In certain embodiments, the present disclosure provides methods for assessing the presence or absence of a pathogen or a pathogen-derived toxin in a sample, comprising providing a plurality of biosensor complexes, each biosensor complex comprising a toll-like receptor (TLR) ligand binding domain conjugated to a solid support, wherein at least one TLR ligand binding domain is different from the other TLR ligand binding domains of the biosensor complexes, wherein each biosensor complex further comprises a cognate ligand bound to the TLR ligand binding domain, providing a sample, contacting the sample to the plurality of biosensor complexes; detecting a change in binding of at least one TLR to its cognate ligand binding domain, wherein a change in binding indicates the presence of a ligand for the TLR ligand binding domain in the sample, and identifying which biosensor complex or complexes bind ligands present in the sample, wherein a decrease in binding of at least one TLR ligand binding domain to its cognate ligand indicates the presence of a pathogen or a pathogen-derived toxin. In certain embodiments, the sample comprises a pharmaceutical composition formulated for parenteral administration to a human subject. In certain embodiments, the sample comprising a therapeutic agent is determined not to be suitable for administration to a subject if a pathogen or pathogen-derived toxin is present in the sample.

In certain embodiments, a solid support used in one or more of the methods disclosed herein comprises a quantum dot. In certain embodiments, the polypeptide is conjugated to the quantum dot. In certain embodiments, the solid support used in one or more of the methods disclosed herein comprises a bead or a gold nanoparticle.

In certain embodiments, the plurality of biosensor complexes used in one or more of the methods disclosed herein are present on an array comprising a plurality of individually addressable areas, wherein each addressable area includes complexes having the same TLR ligand binding domain, and at least two of the individually addressable areas include complexes having different TLR ligand binding domains.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

DESCRIPTION OF THE DRAWINGS

FIG. 11A is a line graph showing excitation and emission spectra of donor (QDot) and acceptor (Alexa647-tagged CpG DNA) fluorophores. Excitation and emission spectra are shown together with the transmittance values of excitation and emission filters that were used for this study. FIG. 11B shows algorithms that were utilized to calculate the FRET efficiency between a donor and acceptor FRET fluorophore pair. FIG. 11C is a line graph showing normalized FRET measurements of FRET between QDot and TLR9/fluorescent CpG-DNA performed in 384-well plates. Alexa647-tagged CpG DNA (B-class, 2006) alone or together with increasing concentrations of unlabeled competitor DNA (B-class, 2006) was mixed together with purified recombinant TLR9-ECD and Qdots. Mixtures were incubated in wells (10 µl) of 384 plates and fluorescence was analyzed by a plate reader after 60 minutes incubation at 24 degrees C.

DETAILED DESCRIPTION OF CERTAIN EMBODIMENTS

Figure 1:
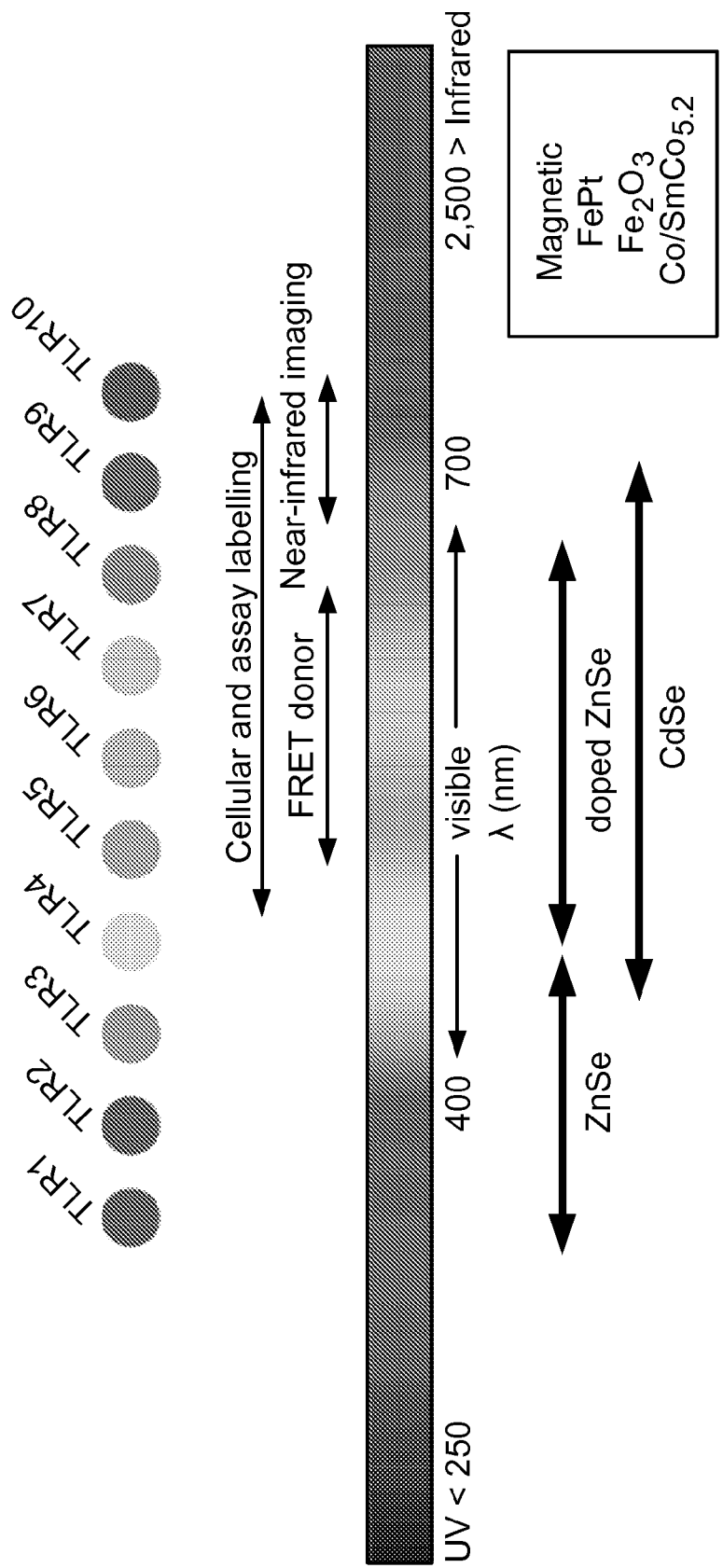
FIG. 1 is a schematic showing the visible electromagnetic radiation spectrum showing regions of fluorescence emission of various quantum dots.

Compositions and methods disclosed herein relate to methods of detecting Toll-like receptor binding to ligands and test compounds.

For most acute and chronic inflammatory diseases, specific diagnostics are often lacking. The immune response in an individual is regularly assessed by crude estimates of immune system activation or depression. For example, body temperature and white blood cell counts are performed to give an overview of the current status of innate immune activation, and levels of acute-phase proteins may be assessed as a further indication of a current inflammatory response. While these tests are undoubtedly important for the assessment of a subject's immune status, few specific markers for the activation of the innate immune system are used in the clinic. On the other hand, a myriad of specific tests for infectious diseases (PCR, specific antibody response, microorganism culture, etc.) or for evaluation of an adaptive immune response (antibody subtype, specific antibody, etc.) are available. Many chronic inflammatory diseases (e.g., sepsis, atherosclerosis, ischemia/reperfusion-mediated organ dysfunction, rheumatoid arthritis, diabetes, and cancer) are based on overly active innate immune receptors that are triggered by unknown ligands or by a combination of various ligands, and specific test to determine which innate immune receptors are active could be highly beneficial.

Furthermore, the immunological response to infectious diseases is different between individuals. At any given timepoint during an infection different amounts and combinations of innate immune receptor stimulating agents may be present, and will vary on an individual basis. For example, under some circumstances acute overly inflammatory responses towards infectious agents can occur leading to the clinical syndrome sepsis and septic shock. The inflammatory response to a variety of innate immune cell stimulants is ultimately dependent on the activation of one or more innate immune receptors. Therefore, it would be of great value to be able to analyze the inflammatory material in samples from a subject.

Toll-like receptor (TLRs) TLRs are transmembrane signaling receptors that can directly bind to cognate ligands. The term "cognate ligands" as used herein in reference to a TLR refers to a ligand that is specifically recognized by a TLR. In certain embodiments, a cognate ligand is a microbial structure (e.g., a naturally occurring microbial structure) that a TLR recognizes and binds to. A wide spectrum of microbial structures that include lipids, e.g. bacterial lipopolysaccharides (recognized by TLR4), lipopeptides (recognized by TLR2), proteins (e.g. flagellin recognized by TLR5) and nucleic acids (recognized via TLR3, 7, 8 and 9) (Akira, S. & Takeda, K., Nat Rev Immunol 4, 499-511, 2004; Kawai, T. & Akira, S., Curr Opin Immunol, 2005, each of which is incorporated by reference in its entirety). Several different TLRs have been identified (see e.g., Takeda et al., 2003, Ann. Rev. Immunol., 21:335-376. Epub 2001 Dec. 19; Barton and Medzhitov, 2002, Curr. Top. Microbiol. Immunol., 270:81-92, each of which is incorporated herein by reference in its entirety). Any TLR polypeptide can be used in accordance with the compositions and methods described herein. In general, TLR nucleic acid sequences are known, and can be cloned and expressed using methods known in the art. Suitable toll-like receptors include, but are not limited to, toll-like receptor 1, Homo sapiens (GeneID: 7096; UniGene Cluster Hs. 111805; NCBI Accession #NP003254.2, AAC34137.1); toll-like receptor 2, Homo sapiens (GeneID: 7097; UniGene Cluster Hs. 519033; NCBI Accession #AAH33756.1, AAM23001.1, AAC34133.1); toll-like receptor 3, Homo sapiens (GeneID: 7098; UniGene Cluster Hs. 29499; NCBI Accession #AAC34134.1, NP003256.1); toll-like receptor 4, Homo sapiens (GeneID: 7099 (var. C); UniGene Cluster Hs. 174312; NCBI Accession #AAC34135.1, AAF89753.1, AAF07823.1, AAF05316.1); toll-like receptor 5, Homo sapiens (GeneID: 7100; UniGene Cluster Hs. 114408; NCBI Accession #AAC34136.1, BAB43955.1); toll-like receptor 6, Homo sapiens (GeneID: 10333; UniGene Cluster Hs. 366986; NCBI Accession #NP006059.2, BAA78631.1); toll-like receptor 7, Homo sapiens (GeneID: 51284; UniGene Cluster Hs. 179152; NCBI Accession #AAF60188.1, AAF78035.1, NP057646.1, AAH33651.1); toll-like receptor 8, Homo sapiens (GeneID: 51311; UniGene Cluster Hs. 272410; NCBI Accession #AAF64061.1, AAF78036.1); toll-like receptor 9 Homo sapiens (GeneID: 54106; UniGene Cluster Hs. 87968; NCBI Accession # AAG01734.1, AAG01735.1, AAG01736.1, BAB19259.1); toll-like receptor 10, Homo sapiens (GeneID: 81793; UniGene Cluster Hs. 120551; NCBI Accession #AAK26744.1, NP112218.1); toll-like receptor 1, Mus musculus (GeneID: 21897; UniGene Cluster Mm. 273024; NCBI Accession #AAG35062.1, AAG37302.1, NP109607.1); toll-like receptor 2, Mus musculus (GeneID: 24088; UniGene Cluster Mm. 87596; NCBI Accession #AAD46481.1, AAF04277.1, AAD49335.1, NP036035.2, AAF28345.1); toll-like receptor 3, Mus musculus (GeneID: 142980; UniGene Cluster Mm. 33874; NCBI Accession #AAK26117.1, AAL27007.1, NP569054.2); toll-like receptor 4, Mus musculus (GeneID: 21898; UniGene Cluster Mm. 38049; NCBI Accession #AAD29272.1, AAF04278.1, AAF05317.1, NP067272.1, AAH29856.1); toll-like receptor 5, Mus musculus (GeneID: 53791; UniGene Cluster Mm. 116894, Mm. 347908; NCBI Accession #AAF65625.1, NP058624.1); toll-like receptor 6, Mus musculus (GeneID: 21899; UniGene Cluster Mm. 42146, Mm. 347552; NCBI Accession #BAA78632.1, AAG38563.1, NP035734.1); toll-like receptor 7, Mus musculus (GeneID: 170743; UniGene Cluster Mm. 23979; NCBI Accession #AAK62676.1, NP573474.1, AAL73191.1, AAL73192.1); toll-like receptor 8, Mus musculus (GeneID: 170744; UniGene Cluster Mm. 196676; NCBI Accession #NP573475.1, AAK62677.1); and toll-like receptor 9, Mus musculus (GeneID: 81897; UniGene Cluster Mm. 44889; NCBI Accession #BAB19260.1, AAK29625.1, AAK28488.1, NP112455.1). Not only do TLRs bind foreign microbial structures, but it is now recognized that certain members of the TLR family also recognize self-epitopes that appear in non-infectious alterations of the normal physiological state, such as epitopes that are either released from dying or damaged cells or are present at the surface of apoptotic cells (Marshak-Rothstein, A. & Rifkin, I. R., Annual review of immunology 25, 419-441, 2007, incorporated by reference in its entirety). It is believed that the ability to recognize host-derived altered molecules is a mechanism to recognize non-infectious tissue damage. Immune cell activation by host-derived material can initiate immune responses that lead to clearance of damaged tissues and can induce tissue repair mechanisms (Matzinger, P., Annual review of immunology 12, 991-1045, 1994; Matzinger, P., Ann NY Acad Sci 961, 341-342, 2002, incorporated by reference in its entirety).

Mutations in mammalian TLRs illustrate that the inability to sense the presence of microorganisms in otherwise sterile compartments can have dramatic consequences for the host (Schroder, N. W. & Schumann, R. R., The Lancet infectious diseases 5, 156-164, 2005, incorporated by reference in its entirety). On the other hand, there is now also increasing evidence that in many acute and chronic inflammatory syndromes excessive or uncontrolled activation of the same receptors form the basis for the pathological state. Examples for TLR-associated inflammatory diseases are common syndromes, such as septic shock syndrome and many auto-immune pathologies and chronic inflammatory diseases (Marshak-Rothstein, A. & Rifkin, I. R., Annual review of immunology 25, 419-441, 2007; Beutler, B., Nature 430, 257-263, 2004; Cook, D. N., Pisetsky, D. S. & Schwartz, D. A., Nature immunology 5, 975-979, 2004; Cristofaro, P. & Opal, S. M., Expert opinion on therapeutic targets 7, 603-612, 2003, each of which is incorporated by reference in its entirety).

Recent progress in the understanding of the basic molecular mechanisms of immune recognition of foreign and altered self-molecules opens the exiting possibility of pharmacological intervention of TLR and other pattern recognition molecule-mediated signaling pathways. The development of specific pharmacological modulators of these important signaling receptors is an important step in the successful treatment of many acute and chronic inflammatory diseases (e.g., sepsis, atherosclerosis, ischemia/reperfusion-mediated organ dysfunction, rheumatoid arthritis, diabetes (e.g., type 2 diabetes). Indeed, several TLR inhibitors and activators have already been identified and have been or are being tested in clinical trials for effectiveness in various TLR-associated diseases. The following are non-limiting examples of TLR inhibitors: TAK-242 (ethyl (6R)-6-[N-(2-chloro-4-fluorophenyl)sulfamoyl]cyclohex-1-ene-1-carboxylate), a small-molecule antisepsis agent, suppresses lipopolysaccharide (LPS)-induced inflammation by selectively inhibiting TLR4 signaling (see e.g., Kawamoto et al., TAK-242 selectively suppresses Toll-like receptor 4-signaling mediated by the intracellular domain, Eur J Pharmacol. 2008 Apr. 14; 584(1): 40-8. Epub 2008 Feb. 5, and Masayuki et al., A novel cyclohexene derivative, ethyl (6R)-6[N-(2-Chloro-4-fluorophenyl)sulfamoyl]cyclohex-1-ene-1-carboxylate (TAK-242), selectively inhibits toll-like receptor 4-mediated cytokine production through suppression of intracellular signaling, Mol Pharmacol. 2006 April; 69(4):1288-95. Epub 2005 Dec. 22, each of which is incorporated herein by reference in its entirety). Eritoran (E5564), Alpha-D-glucopyranose, 3-O-decyl-2-deoxy-6-O-[2-deoxy-3-O-[(3R)-3-methoxydecyl]-6-O-methyl-2-[[(11Z)-1-oxo-11-octadecenyl]amino]-4-O-phosphono-beta-D-glucopyranosyl]-2-[(1,3-dioxotetradecyl)amino]-1-(dihydrogen phosphate), tetrasodium salt, is a synthetic lipodisaccharide that antagonizes the toxic effects of endotoxin, a major immunostimulatory component of the outer cell membrane of Gram negative bacteria, by antagonizing TLR4 (see e.g., Mullarkey et al., Inhibition of endotoxin response by e5564, a novel Toll-like receptor 4-directed endotoxin antagonist, J Pharmacol Exp Ther. 2003 March; 304(3):1093-102, incorporated herein by reference in its entirety). OPN-305 is a TLR2-specific humanized antibody marketed by Opsana that inhibits TLR2 mediated pro-inflammatory cytokine production and is useful in the treatment of multiple diseases, including cardiac and kidney ischemia/reperfusion injuries, sepsis, diabetes, lupus and Alzheimers Disease (see e.g., www.opsona.com and WO/2009/000929, published Dec. 31, 2008 (describing a monoclonal anti TLR2-specific antibody), each of which is incorporated herein by reference in its entirety). IRS 954, a specific oligonucleotide inhibitor of TLR7 and TLR9 (5'-TGCTCCTGGAGGGGTTGT-3'[SEQ ID NO: 1], led to reduction of autoantibody production and amelioration of disease symptoms when administered to lupus-prone mice (see e.g., Barrat et al, Treatment of lupus-prone mice with a dual inhibitor of TLR7 and TLR9 leads to reduction of autoantibody production and amelioration of disease symptoms, Eur J Immunol. 2007 December; 37(12):3582-6, and Barrat et al., Nucleic acids of mammalian origin can act as endogenous ligands for Toll-like receptors and may promote systemic lupus erythematosus, J Exp Med. 2005 Oct. 17; 202(8): 1131-1139, each of which is incorporated herein by reference in its entirety). CPG 52364, a small molecule TLR antagonist designed to specifically inhibit TLRs 7, 8 and 9 for use in the treatment of Systemic Lupus Erythematosus (SLE) has been tested in Phase I clinical trials (see e.g., WO/2008/152471, published Dec. 18, 2008, incorporated herein by reference in its entirety). IMO-3100 is a DNA-based antagonist of TLR7 and TLR9 that inhibits immune responses mediated by TLR7 and TLR9 (Jiang et al., IMO-3100, an Antagonist of Toll-Like Receptors 7 and 9, Modulates Gene Expression and Regulatory Networks Induced by Ligands, The Journal of Immunology, 2009, 182, 48.25, meeting abstract, incorporated herein by reference in its entirety). These and other TLR inhibitors can be used in accordance with methods described herein. Those skilled in the art will be aware of other suitable TLR inhibitors. Caution should be exercised, however, as the exact etiology and the disease precipitating stimulant remain largely unknown for most acute and chronic inflammatory diseases. Thus, a dilemma is evolving in that specific pharmacological immune response modulators are generated but diagnostic means are lacking which aid in the decision making process of which pharmacological agent to utilize in a given inflammatory state.

TLRs have evolved to bind and signal to a great variety of molecules, many of which have not yet been identified. However, if these receptors themselves are functionalized for the use in biosensors, it is, in fact, not necessary to identify the exact nature of the stimulating ligand. In certain embodiments, compositions and methods disclosed herein are useful in determining to which TLR an unknown ligand binds.

As will be recognized by those skilled in the art, it would be advantageous to identify which one or more specific TLRs or other signaling molecules are engaged by ligands that are present in material derived from subjects. The ability to diagnose TLR stimulatory activity in fluids or other samples derived from an individual suffering from an acute or chronic inflammatory disease is advantageous in a variety of clinical uses, e.g. to guide in the selection of therapeutic options. Additionally or alternatively, the ability to diagnose TLR stimulatory activity in fluids or other samples derived from an individual could be used to help stratify subjects for clinical trials. Additionally or alternatively, the ability to diagnose TLR stimulatory activity in fluids or other samples derived from an individual can enable longitudinal assessments of inflammatory materials in subjects, which would help in the development of a rational individualized treatment of inflammatory diseases. In certain embodiments, compositions and methods disclosed herein are useful in detecting to which specific TLR or TLRs are bound by a ligand present in a given body fluid of a subject or in other fluids.

TLRs bind to signaling molecules, e.g. ligands such as microbial structures that include lipids and self-epitopes.

Binding by such ligands activates signaling pathways that help the cell defend against invading microbes and/or clear damaged tissues and induce tissue repair mechanisms.

Methods for detecting a ligand that binds a toll-like receptor are disclosed herein. In certain embodiments, such methods comprise use of a biosensor complex. As used herein, the term "biosensor complex" refers to a complex comprising a polypeptide conjugated to a solid support, and a cognate ligand that binds the polypeptide. Any of a variety of solid supports can be used to form a biosensor complex. Exemplary solid supports include, without limitation, quantum dots and gold nanoparticles. In certain embodiments, the solid support is detectably labeled. For example, a solid support can be labeled with a fluorescent label. A wide variety of fluorescent labels is known in the art and can be used in accordance with the compositions and methods disclosed herein. Exemplary fluorescent labels include, without limitation, Alexa Fluor 350, Alexa Fluor 405, Alexa Fluor 430, Alexa Fluor 488, Alexa Fluor 532, Alexa Fluor 532, Alexa Fluor 546, Alexa Fluor 555, Alexa Fluor 568, Alexa Fluor 594, Alexa Fluor 647, Alexa Fluor 660, Alexa Fluor 680, AMCA, BODIPY 630/650, BODIPY 650/665, BODIPY-FL, BODIPY-R6G, BODIPY-TMR, BODIPY-TRX, carboxyfluorescein, Cascade Blue, Cy3, Cy5, Cy5.5, 6-FAM, Fluorescein, HEX, 6-JOE, Lissamine rhodamine B, Oregon Green 488, Oregon Green 500, Oregon Green 514, Pacific Blue, REG, Rhodamine Green, Rhodamine Red, ROX, SpectrumAqua, TAMRA, TET, Tetramethylrhodamine, and Texas Red. Those of ordinary skill in the art will be aware of other suitable fluorescent labels.

In certain embodiments, a polypeptide in a biosensor complex comprises a Toll-like receptor (TLR). Ligands typically bind to the extracellular portion of TLRs. In certain embodiments, a polypeptide in a biosensor complex comprises a TLR ligand binding domain. As used herein, the term "TLR ligand binding domain" refers to any portion of a TLR that is extracellular under normal physiological conditions, and that is capable of binding at least one ligand. TLR ligand binding domains are characterized by the presence of two regions of leucine rich repeats (LRR), a common motif of about twenty amino acids with several leucine residues located at fixed intervals, in the N-terminal ("extracellular") domain and a toll interleukin 1 resistance (TIR) domain in the intracellular portion (see, e.g., Bell et al., 2003, Trends Immunol., 24(10): 528-33, incorporated herein by reference in its entirety). TLR ligand binding domains typically consist of several LRRs, including several glycosylation consensus sequences. In certain embodiments, a TLR ligand binding domain comprises the whole extracellular domain of a given toll-like receptor. It is thought that the LRRs are also responsible for protein-protein interactions. Stretches of LRRs confer a horseshoe shape to the LRR-containing polypeptide, by forming alpha helices facing the external surface and beta sheets defining a hydrophobic core. The structure of TLR3 was published in Bell et al., Proc Natl Acad Sci USA. 102(31): 10976-10980, 2005, incorporated herein by reference in its entirety. Intervening amino acid sequences interspersed among the LRR are thought to be responsible for conferring ligand binding specificity; they usually reside in the beta sheet side of the molecule. TLR ligand binding domains are heavily N-glycosylated and possess a high number of cysteine residues. Both these characteristics are thought to stabilize the horseshoe fold and contribute to the ligand binding specificities. The structures and amino acid sequences of various TLRs are known in the art, and those of ordinary skill will be aware of and will be able to recognize a TLR ligand binding domain.

As one non-limiting example, the general architecture of the TLR9 amino acid sequence [MGFCRSALHPLSLLVQAIM-LAMTLALGTLPAFLPCELQPHGLVNCN-WLFLKSVPHF SMAAPRGNVTSLSLSSNRIHHLHDSD-FAHLPSLRHLNLKWNCPPVGLSPMHFPCHMT IEPSTFLAVPTLEELNLSYNNIMTV-PALPKSLISLSLSHTNILMLDSASLAGLHAIRFLF MDGNCYYKNPCRQALEVAPGALLGLGN-LTHLSLKYNNLTVVPRNLPSSLEYLLLSY NRIVKLA-PEDLANLTALRVLDVGGNCRRCDHAPN-PCMECPRHFPQLHPDTFSHLSRL EGLVLKDSSLSWLNASWFRGLGNLRV-LDLSENFLYKCITKTKAFQGLTQLRKLNLSF NYQKRVSFAHLSLAPSFGSLVALKELDM-HGIFFRSLDETTLRPLARLPMLQTLRLQM NFIN-QAQLGIFRAFPGLRYVDLSDNRISGAS-ELTATMGEADGGEKVWLQPGDLAPAP VDTPSSEDFRPNCSTLN-FTLDLSRNNLVTVQPEMFAQLSHLQCL-RLSHNCISQAVNGS QFLPLTGLQVLDLSHNKLDLY-HEHSFTELPRLEALDLSYNSQPFGMQGVGHNFSFVA HLRTLRHLSLAHNNIHSQVSQQLCSTSL-RALDFSGNALGHMWAEGDLYLHFFQGLS GLI-WLDLSQNRLHTLLPQTLRNLPKSLQVLR-LRDNYLAFFKWWSLHFLPKLEVLDLA GNQLKALTNGSLPAGTRLRRLDVSCNS-ISFVAPGFFSKAKELRELNLSANALKTVDH SWFG-PLASALQILDVSANPLHCACGAAFMD-FLLEVQAAVPGLPSRVKCGSPGQLQG LSIFAQDLRLCLDEALSWDCFALSLLA-VALGLGVPMLHHLCGWDLWYCFHLCLAW LPWR-GRQSGRDEDALPYDAFVVFDKTQSAVAD-WVYNELRGQLEECRGRWALRLCL EERDWLPGKTLFENLWASVYGSRKTLFV-LAHTDRVSGLLRASFLLAQQRLLEDRKD VVVLVIL-SPDGRRSRYVRLRQRLCRQSVLLW-PHQPSGQRSFWAQLGMALTRDNHHF YNRNFCQGPTAE] (SEQ ID NO: 2) comprises an extracellular region which includes two leucine-rich repeat (LRR) regions, e.g., amino acids 64-435 (LRR region 1) and 473-750 (LRR region 2) of SEQ ID NO: 2; a single transmembrane domain, e.g., amino acids 819-839 of SEQ ID NO: 2; and then the TIR domain (Toll/IL-1 Resistance signaling domain) at the C-terminus, e.g., amino acids 868-1016 of SEQ ID NO: 2 (see e.g., Akira, Curr. Opin. Immunol. 15:5-11, 2003, incorporated herein by reference in its entirety). TLR9 also contains a signal sequence, e.g., amino acids 1-25 of SEQ ID NO: 2. In general, regions of a TLR9 containing a COX motif, e.g., CRRC at amino acids 255-258 of SEQ ID NO: 2 or CMEC at amino acids 265-268 of SEQ ID NO: 2, are potential nucleic acid ligand binding domains, e.g., for CpG-DNA. Extracellular and ligand binding domains of other TLRs have been identified and are known in the art. See, e.g., Ozinsky et al., PNAS 97(25):13766-13771 (2000).

A cognate ligand to be used in accordance with the compositions and methods disclosed herein will depend on the particular TLR or TLR ligand binding domain present in a biosensor complex. As is known to those skilled in the art, various TLRs exhibit specificities for individual ligands. As one non-limiting example, TLR9 is known to bind CpG DNA. Thus, in certain embodiments, a biosensor complex comprises a TLR9 or a TLR9 ligand binding domain and CpG DNA. As another non-limiting example, TLR2 is known to bind to lipidated peptides such as Pam2CysK4. Those of ordinary skill in the art will be aware of particular ligands known to bind particular TLRs, and will be able to use such ligand and TLRs in accordance with the compositions and methods disclosed herein.

In certain embodiments, a cognate ligand can be detectably labeled. For example, a cognate ligand can be labeled with a fluorescent label. A wide variety of fluorescent labels is known in the art and can be used in accordance with the compositions and methods disclosed herein. Exemplary fluorescent labels include, without limitation, Alexa Fluor 350, Alexa Fluor 405, Alexa Fluor 430, Alexa Fluor 488, Alexa Fluor 532, Alexa Fluor 532, Alexa Fluor 546, Alexa Fluor 555, Alexa Fluor 568, Alexa Fluor 594, Alexa Fluor 647, Alexa Fluor 660, Alexa Fluor 680, AMCA, BODIPY 630/650, BODIPY 650/665, BODIPY-FL, BODIPY-R6G, BODIPY-TMR, BODIPY-TRX, carboxyfluorescein, Cascade Blue, Cy3, Cy5, Cy5.5, 6-FAM, Fluorescein, HEX, 6-JOE, Lissamine rhodamine B, Oregon Green 488, Oregon Green 500, Oregon Green 514, Pacific Blue, REG, Rhodamine Green, Rhodamine Red, ROX, SpectrumAqua, TAMRA, TET, Tetramethylrhodamine, and Texas Red. Those of ordinary skill in the art will be aware of other suitable fluorescent labels.

In certain embodiments, both a solid support and a cognate ligand are detectably labeled, e.g. fluorescently labeled. In certain embodiments, fluorescent labels present on a solid support and a cognate ligand are chosen such that it is possible to determine whether the cognate ligand is part of a biosensor complex, e.g. by virtue of being bound to a TLR or TLR ligand binding domain. As is known to those of ordinary skill in the art, fluorophores exhibit characteristic electromagnetic absorption and emission spectra. In certain embodiments, fluorescent labels are chosen such that the emission spectrum of one overlaps with the absorption spectrum of another (a phenomenon commonly termed Fluorescent Resonance Energy Transfer, or "FRET"). FRET occurs when the fluorescent labels are spatially close enough to one another such that a recipient fluorophore is able to absorb the emission radiation from a donor fluorophore. The further away the two fluorophores are from each other, the less efficient the energy transfer. Thus, FRET is a useful technique to measure proximity of two fluorescently-labeled molecules.

In certain embodiments, the emission spectrum of a fluorescent label present on a solid support can overlap with the absorption spectrum of a fluorescent label present on a cognate ligand. In such embodiments, excitation of the fluorescent label present on a solid support will result in excitation of the fluorescent label present on a cognate ligand. Thus, it is possible to determine whether a cognate ligand is present in a biosensor complex by measuring an increase in the emission spectrum of the cognate ligand fluorophore upon excitation of the solid support fluorophore. Additionally or alternatively, since at least a portion of the emission spectrum of the solid support fluorophore will be absorbed by the cognate ligand fluorophore, it is possible to determine whether a cognate ligand is present in a biosensor complex by measuring a decrease in the emission spectrum of the solid support fluorophore upon excitation.

In certain embodiments, a cognate ligand comprises a quencher. A quencher is a molecule that absorbs electromagnetic radiation but, in contrast to a fluorescer, does not emit electromagnetic radiation (or emits very low levels of electromagnetic radiation) upon absorption. A wide variety of quenchers is known in the art and can be used in accordance with the compositions and methods disclosed herein. Exemplary quenchers include Black Hole Quencher Dyes (see e.g., U.S. Pat. No. 7,109,312, incorporated by reference in its entirety). Those of ordinary skill in the art will be aware of other quenchers that can be used in accordance with the compositions and methods disclosed herein. In certain embodiments, a fluorescent label present on a solid support and a quencher are chosen such that it is possible to determine whether the cognate ligand is part of a biosensor complex, e.g. by virtue of being bound to a TLR or TLR ligand binding domain. In certain embodiments, a fluorescent label on a solid support is chosen such that its emission spectrum overlaps with the absorption spectrum of a quencher on a cognate ligand. In such embodiments, it is possible to determine whether a cognate ligand is present in a biosensor complex by measuring a decrease in the emission spectrum of the solid support fluorophore upon excitation.

In certain embodiments, methods disclosed herein comprise contacting a biosensor complex with a sample known or suspected to contain a test ligand. As used herein, the term "test ligand" refers to a ligand that is suspected of binding to a polypeptide of the biosensor complex, e.g. a TLR or TLR ligand binding domain. In certain embodiments, a test ligand is the same as a cognate ligand used to form a biosensor complex. It is not necessary, however, that the test ligand be the same as the cognate ligand, so long as the cognate ligand and test ligand compete for binding to the TLR or TLR ligand binding domain. Such competition may be direct (e.g., binding the ligand binding domain). Alternatively, such competition may be indirect. For example, binding by one ligand at the ligand binding domain may interfere with binding by a second ligand at a different ligand binding domain.

In certain embodiments, binding by a test ligand displaces a previously bound cognate ligand, and a decrease in binding of the cognate ligand is detected. Such displacement can be detected by use of suitable fluorescent labels and quenchers as described herein. For example, a fluorescently labeled cognate ligand will emit characteristic radiation upon excitation of a fluorescently labeled solid support when the emission and absorption spectra overlap. Upon displacement of the fluorescently labeled cognate ligand by the test ligand, a difference in fluorescence can be detected. For example, upon such displacement, excitation of the fluorophore on the solid support will result in a decrease in the emission spectrum of the fluorescently labeled cognate ligand and a concomitant increase in the emission spectrum of the fluorescently labeled solid support (due to the fact that its emission radiation is not absorbed, or is absorbed to a lesser extent, by the cognate ligand fluorophore). As another example, a decrease in binding of a cognate ligand labeled with a quencher can be detected by detecting an increase in the fluorescence of a fluorescently labeled solid support upon displacement of the cognate ligand by the test ligand.

Figure 9:
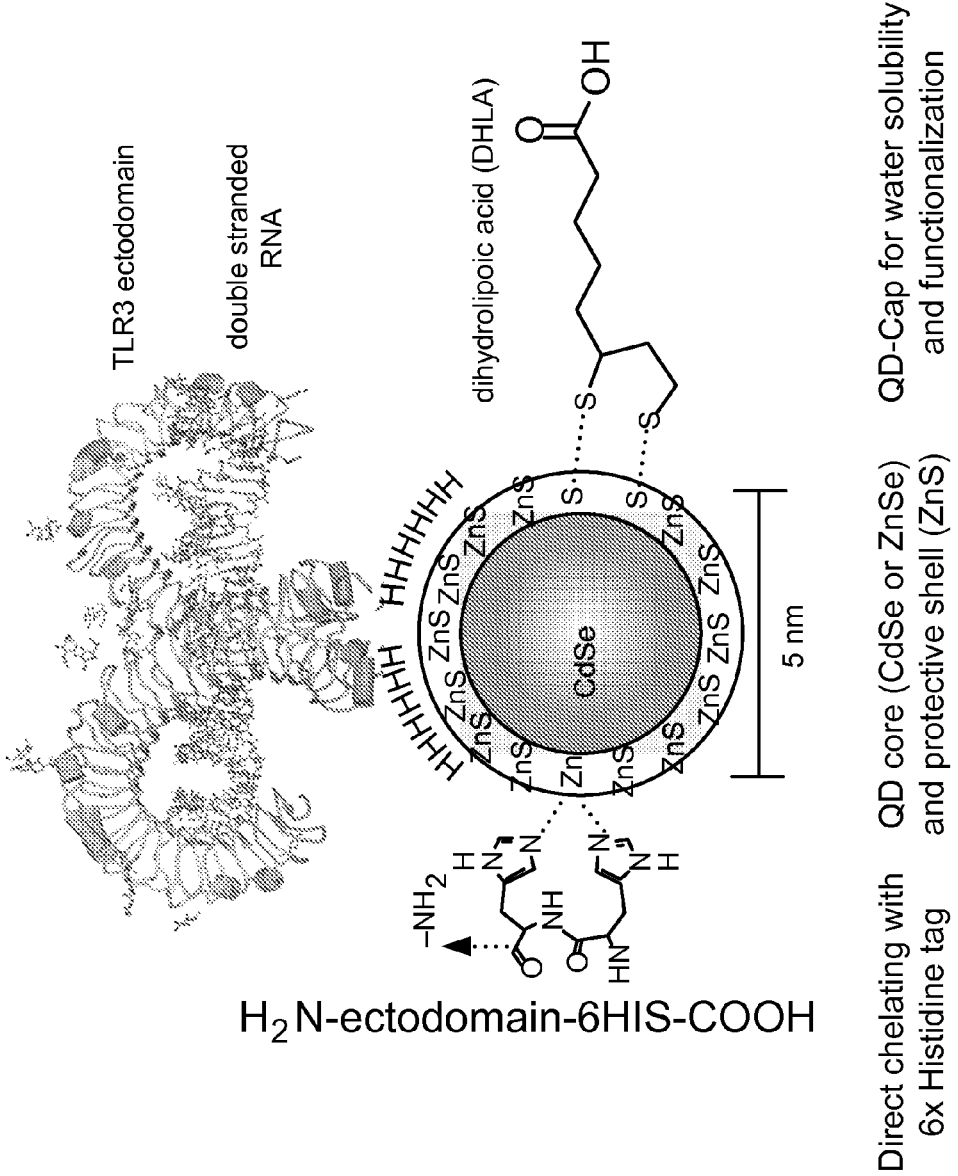
FIG. 9 is a schematic illustration of an example of a CdSe QDot in scale with the co-crystal of TLR3 ectodomain with double stranded RNA. As shown, the Qdot is also conjugated to dihydrolipoic acid (DHLA) and a 6His tag.

In certain embodiments, a TLR or a fragment that includes a TLR ligand binding domain is conjugated to a quantum dot for use in detecting binding by a ligand. In certain embodiments, a TLR or a fragment that includes a TLR ligand binding domain is conjugated to a fluorescent quantum dot for use in detecting binding by a ligand. Quantum dots are semiconducting nanocrystals are 1-10 nm large inorganic particles with unique size-dependent optical and electrical properties due to quantum confinement. Quantum dots typically include atom clusters comprising a core, shell and coating. FIG. 9 shows an example of a CdSe QDot in scale with the co-crystal of TLR3 ectodomain with double stranded RNA. The core is often made up of a few hundred to thousand atoms of semiconductor material (e.g., ZnSe or CdSe) and a ZnS semiconductor shell often is used to surround and stabilize the core. See also, Quantum dots Watson et al., BioTechniques 2003 February; 34(2):296-300, 302-3; Goldman et al., J. Am. Chem. Soc. 2002 Jun. 5; 124(22):6378-82; Han et al., Nat.

Biotechnol. 2001 July; 19(7):631-5; and Chan et al., Science 1998 Sep. 25; 281(5385):2016-8, each of which is incorporated by reference in its entirety.

Fluorescent quantum dots such as ZnSe or CdSe containing nanomaterial have a variety of properties that are beneficial for application in biological systems. Among these properties are a high quantum yield, high molar extinction coefficients (~10-100 times that of organic dyes), broad absorption with narrow, symmetric photoluminescence (PL) spectra spanning the UV to near-infrared (see e.g., FIG. 1) spectrum, large effective stokes shifts, high resistance to photobleaching and exceptional resistance to photo and chemical degradation. Thus, fluorescent quantum dots exhibit several characteristics that are especially beneficial for the development of biosensors based on fluorescence.

Figure 2:
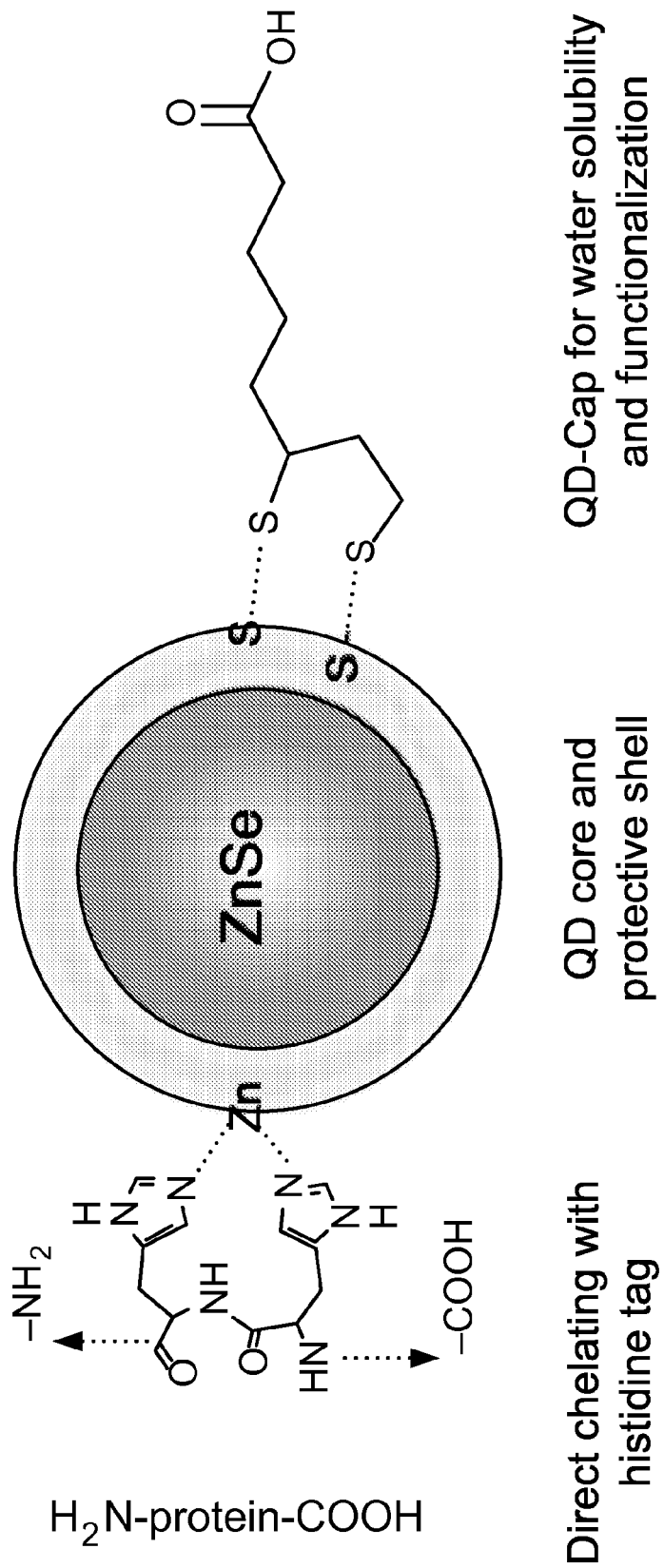
FIG. 2 is a schematic illustration of an exemplary surface-functionalization of quantum dots.

Quantum dots are produced in a hydrophobic environment, so in order to be able to use them in biological applications they have to be made water-soluble (see e.g., FIG. 2). In certain embodiments, quantum dots are made water-soluble by utilizing an amphipathic coating, e.g., a long carbon-chain carboxyl acids functionalized with bi-dentate thiol-groups (e.g. DHLA, dihydrolipoic acid) that are coupled to surface sulfurs in the ZnS-shell (protecting the CdSe/ZnSe-core). The thiol groups can couple to surface sulfurs in the ZnS-shell. The coating can contain many different functional groups for chemical linkage of biomolecules. After water-solubilization, a variety of biological conjugation can be used. In certain embodiments, polypeptides can be conjugated to a quantum dot covalently. For example, one can use normal chemical reagents (e.g., EDC, a carbodiimide derivative) to directly and covalently link proteins to the DHLA carboxyl acid groups through available amino-groups. Such a method also provides the possibility to couple any other molecules that have or was introduced with amino-groups, e.g. DNA or PEG. In certain embodiments, polypeptides can be conjugated to a quantum dot noncovalently. For example, biological conjugation can be achieved by noncovalent self-assembly between DHLA-capped quantum dots and proteins appended with a polyhistidine tag (e.g., such as a tag that is used regularly in protein-purification techniques). Such an approach takes advantage of the strong chelating affinity of the polyhistidine (6xHis) tag towards transition metal ions (e.g. $Ni^{2+}$ and $Zn^{2+}$), and can be advantageous in that self-assembly of the hybrid material can be controlled. Moreover, such non-covalent self-assembly avoids issues with non-specific assembly that could potentially interfere with ligand binding.

In certain embodiments, quantum dots can be surface coated with polyethylene glycol (e.g., PEG(1100)) in order to reduce the overall charge of the material. Such embodiments can be advantageous for binding of certain TLR polypeptides and TLR extracellular binding domain polypeptides to the quantum dot material when the negative charge of the DHLA interacts with or otherwise interferes with the binding site of the TLR biding domain. For example, TLR9 binds CpG DNA. In certain embodiments, polyethylene glycol is used to coat quantum dots to avoid DHLA from interacting or interfering with the DNA binding site on the TLR9 polypeptide.

Batches of nanomaterial can be tested as follows. Known concentrations of fluorescent 6His containing test peptides (e.g., A647K-P5-H6 and A647K-P15-H6) can be mixed at different molar ratios with quantum dots and their binding assessed by agarose electrophoretic mobility shift assay (EMSA). After electrophoresis, the gel can be analyzed for fluorescence using different excitation and emission filters adjusted to the fluorescence of quantum dot and peptide using a fluorescent gel-reader system (e.g., FluorChem HD2 with ChromaLight multiwavelength illuminator, ALPHAINNOTECH). The amount of binding and the saturation of binding sites can be estimated by using increasing ratios of peptide to quantum dot.

In certain embodiments, a biosensor complex is formed by mixing a 6His-tagged TLR polypeptide or TLR ligand binding domain polypeptide, the nanomaterial (e.g. quantum dots) and fluorescent reference DNA ligands. In some embodiments, it will be advantageous to mix together the TLR polypeptide or TLR ligand binding domain polypeptide and nanomaterial at various optimized molar ratios. Those of ordinary skill in the art will be able to determine such optimized molar ratios using any of a variety of methods disclosed herein and known in the art. In certain embodiments, assembly of the biosensor is achieved by mixing optimal molar ratios of quantum dot, protein and fluorescent ligand together.

Figure 3:
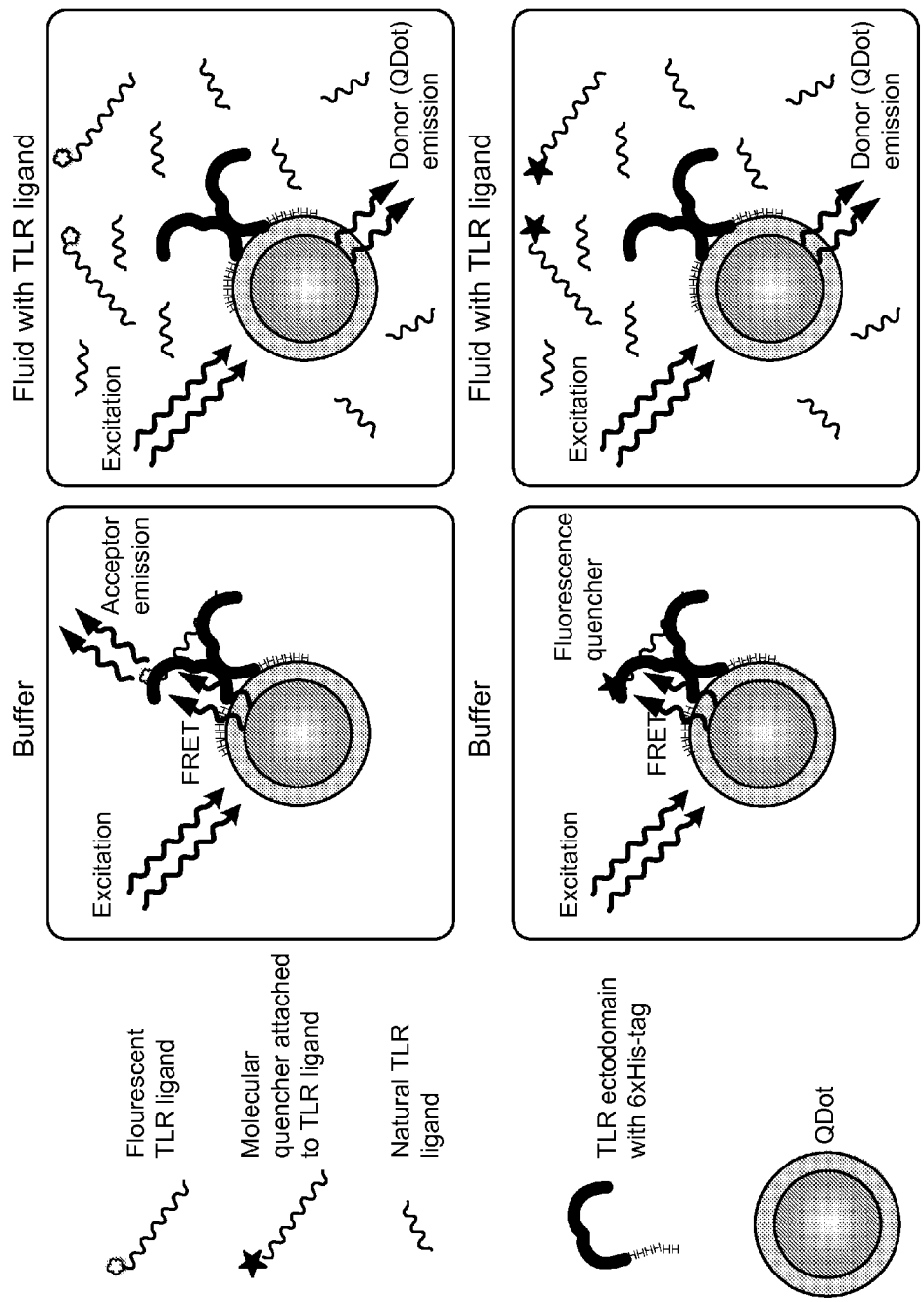
FIG. 3 is a schematic illustration of exemplary FRET-based readout strategies for quantum dot biosensors.
Figure 4:
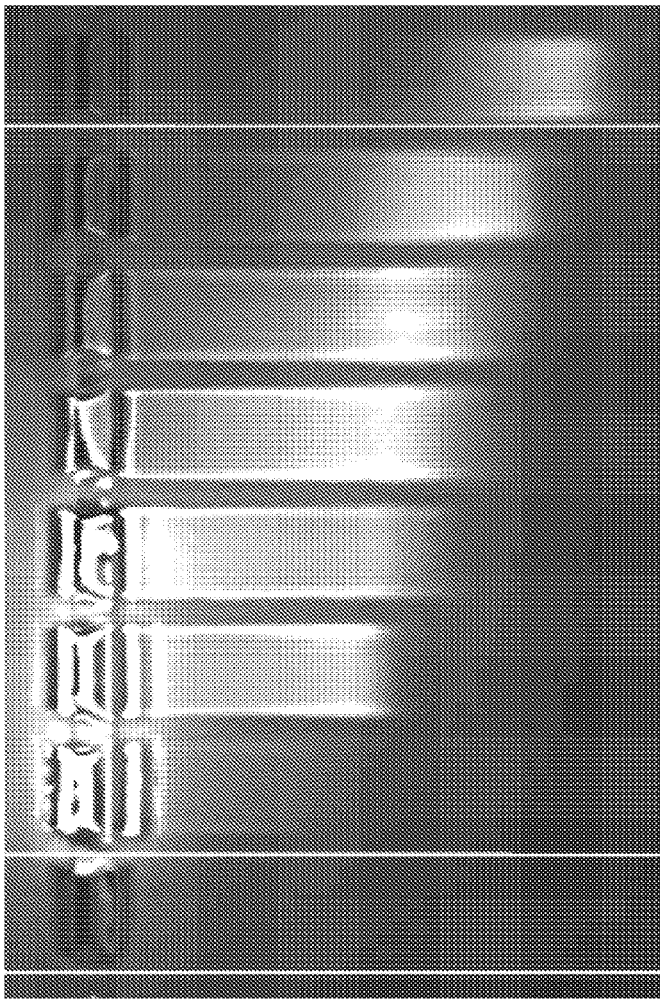
FIG. 4 is a photograph of an agarose gel showing binding of mRAGE-His to QDot550-DHLA in increasing ratio. Green color (observed in the color photograph) represents the fluorescence emission of QDot550.

In certain embodiments, fluorescent quantum dots are functionalized with TLR or the extracellular domains of various TLRs as 6xHis-tagged proteins and use the self-assembly technique via Zn-to-histidine coordination as described above to achieve biosensors. In certain embodiments, the readout for ligand binding to the TLR9 or TLR9 extracellular domain of the bound TLR can be a FRET-based technique (see e.g. FIG. 3). In certain embodiments, fluorescent nanomaterial that emits at a wavelength that is optimally overlapping with the excitation spectrum of a dye that is physically bound to a model TLR ligand is used. For example, a quantum dot-bound TLR9 or TLR9 extracellular domain can bind such a fluorescent ligand to achieve a FRET signal. TLR ligands that are present in test fluids or subject derived materials will compete for the binding with the fluorescent model ligand and decrease the amount of FRET.

An alternative assay set-up is achieved by utilizing a fluorescence quencher dye attached to the model TLR ligand instead of a FRET acceptor molecule. In this set-up, the increase of quantum dot-derived overall fluorescence signal (rather than the decrease of specific FRET signal) is used as the read-out for ligand binding to the TLR polypeptide or TLR ligand binding domain that is bound to the quantum dot.

As the fluorescence spectra of quantum dots can be tuned by increasing the size of the quantum dot material, it is possible to set up multiplexed assay systems, where the color code of fluorescence indicates the type of molecule attached to the surface of the quantum dot material. It is thus possible to probe for multiple TLR ligands simultaneously which can dramatically increase the throughput and applicability of these biosensor devices for clinical testing.

The dimension of matter defining the nanotechnology field is typically in the range of 0.2 to 100 nm. At this scale, the surface-to-volume ratios of materials become large and their electronic energy states become discrete. This can lead to unique optical, electronic, magnetic and mechanical properties, which can substantially differ from those in the bulk. For example, gold (Au) is chemically inert in the bulk but catalytically active as a nanoparticle, and metal chalcogenide chemical compounds are highly luminescent as nanoparticles but nonluminescent in the bulk.

Gold nanoparticles are different from quantum dots in that they are not inherently fluorescent. Gold nanoparticles, however, exhibit very strong absorbance and efficiently scatter light, both of which are dependent on the size of the gold particle. Because of the strong absorbance, very small (e.g. few-nanometer-sized) gold particles are natural fluorescence quenchers. This feature can be utilized for biosensing the same way as is described above for quantum dots, except that the gold will act as a quencher and a competing fluorescently-labeled ligand will give the readout signal. In certain embodiments, the surface of the gold particle is functionalized with Ni2+-NTA-containing long acyl- or PEG-chains, then a 6×His-tagged polypeptide (e.g., a TLR or a TLR extracellular domain) can be coupled efficiently to the nanoparticle.

In certain embodiments, compositions and methods disclosed herein can be used in clinical applications. For example, compositions and methods disclosed herein can be used to diagnose certain disease conditions and/or infections. Disease conditions and/or infections that affect TLR signaling are often caused by unknown ligands or by a combination of various ligands, and specific test to determine which innate immune receptors would be highly beneficial. In certain embodiments, a sample from a subject suffering from a disease or infection (e.g., an inflammatory condition) is tested using one or more biosensor complexes described herein. Such a sample, for example, can contain a ligand that affects one or more TLRs such that symptoms of the disease or infection result. In certain embodiments, a sample contains, or is derived from, amniotic fluid, blood, blood cells, cerebrospinal fluid, fine needle biopsy samples, peritoneal fluid, plasma, pleural fluid, saliva, semen, serum, sputum, tissue or tissue homogenates, tissue culture media, and/or urine.

In certain embodiments, methods of diagnosing a gram negative or gram positive infection in a subject (e.g., a human) are provided. Gram negative bacteria are known to comprise lipopolysaccharides (LPSs) that interact with TLR4 (see e.g., Roger et al., Protection from lethal gram-negative bacterial sepsis by targeting Toll-like receptor 4, Proc Natl Acad Sci USA. 2009 Feb. 17; 106(7):2348-52. Epub 2009 Jan. 30, incorporated herein by reference in its entirety). Similarly, gram positive bacteria are known to comprise certain lipoproteins that interact with TLR2 (see e.g., Takeda et al., Differential roles of TLR2 and TLR4 in recognition of gram-negative and gram-positive bacterial cell wall components, Immunity. 1999 October; 11(4):443-51, incorporated herein by reference in its entirety). Thus, by detecting whether a sample from a subject includes a ligand that binds either TLR4 or TLR2, it will be possible to determine whether that subject is infected with a gram negative or gram positive bacteria, respectively. In certain embodiments, methods of diagnosing a gram negative or gram positive infection in a subject provided herein comprise providing a plurality of biosensor complexes, each biosensor complex comprising a toll-like receptor (TLR) ligand binding domain conjugated to a solid support and bound to a cognate ligand, wherein at least one biosensor complex comprises a TLR2 ligand binding domain and at least one biosensor complex comprises a TLR4 ligand binding domain. By contacting the plurality of biosensor complexes with a sample from the subject and detecting whether or not one or more of the cognate ligands are displaced (e.g., by detecting a decrease in binding between one or more TLRs and their cognate ligands on biosensor complexes), it is possible to determine whether the sample includes ligands that interact with TLR4 (indicating the presence of gram negative bacteria) or with TLR2 (indicating the presence of gram positive bacteria) in the sample. In certain embodiments, the solid supports, the cognate ligands, or both can be fluorescently labeled, and FRET can be used to detect displacement of the cognate ligands, as described more fully herein.

In certain embodiments, methods are provided for determining the presence of bacteria (e.g., lysed bacteria) in a sample from a subject (e.g., a human). For example, TLR9 is known to bind CpG oligodeoxynucleotides, which are short single stranded DNA molecules that contain a cytosine "C" followed by a guanine "G". Unmethylated CpG motifs act as immunostimulants (see e.g., Weiner et al., Immunostimulatory oligodeoxynucleotides containing the CpG motif are effective as immune adjuvants in tumor antigen immunization, Proceedings of the National Academy of Sciences of the United States of America 94 (20): 10833-7, 1997, incorporated herein by reference in its entirety). CpG motifs are abundant in microbial genomes but rare in vertebrate genomes, and their presence in a subject (e.g., a sample from a subject) is thus indicative of bacterial infection. In certain embodiments, methods for determining the presence of bacteria (e.g., lysed bacteria) in a sample from a subject comprise providing a plurality of biosensor complexes, each biosensor complex comprising a toll-like receptor (TLR) ligand binding domain conjugated to a solid support and bound to a cognate ligand, wherein at least one biosensor complex comprises a TLR9 ligand binding domain. By contacting the plurality of biosensor complexes with a sample from the subject and detecting whether or not the TLR9 cognate ligand is displaced (e.g., by detecting a decrease in binding between TLR9 and its cognate ligand on a biosensor complex), it is possible to determine whether the sample includes ligands that interact with TLR9, indicating the presence of bacteria (e.g., lysed bacteria) in the sample. In certain embodiments, the solid supports, the cognate ligands, or both can be fluorescently labeled, and FRET can be used to detect displacement of the cognate ligands, as described more fully herein.

In certain embodiments, methods for selecting a treatment for a subject (e.g., a human) having an inflammatory condition are provided. An "inflammatory condition" as the term is used herein refers to a disease or condition caused or mediated by one or more innate immune receptors. As described above, many chronic inflammatory conditions (e.g., sepsis, shock, autoimmune pathologies) are based on overly active innate immune receptor(s) that are triggered by unknown ligands, and specific test to determine which innate immune receptors are being stimulated would be highly beneficial. The development of specific pharmacological modulators of these important signaling receptors is an important step in the successful treatment of many acute and chronic inflammatory diseases. Several such modulators are described in detail above.

In certain embodiments, methods for selecting a treatment for a subject (e.g., a human) having an inflammatory condition comprise providing a plurality of biosensor complexes, each biosensor complex comprising a toll-like receptor (TLR) ligand binding domain conjugated to a solid support and bound to a cognate ligand, wherein at least one TLR ligand binding domain is different from the other TLR binding domains of the biosensor complexes. By contacting the plurality of biosensor complexes with a sample from the subject and detecting whether or not one or more of the cognate ligands are displaced (e.g., by detecting a decrease in binding between one or more TLRs and their cognate ligands on biosensor complexes), it is possible to determine whether the sample includes ligands that interact with specific TLRs in the sample. The plurality of biosensor complexes can include any of the variety of TLRs. For example, the plurality of biosensor complexes can include complexes containing one or more of TLR2, TLR4, TLR7, TLR8, and TLR9, each TLR in the plurality of biosensor complexes being bound to a cognate ligand. By determining that one or more cognate ligand is displaced, it is possible to determine whether the sample contains ligands specific for one or more of TLR2, TLR4, TLR7, TLR8, or TLR9, and to choose a suitable treatment for the subject. In certain embodiments, a selected treatment comprises administration of a therapeutic agent to the subject. As described in more detail above, several therapeutic agents that specifically antagonize one or more TLRs are known (e.g., TAK-242 and eritoran are small molecules specific that specifically antagonize TLR4, OPN-305 is a TLR2-specific humanized antibody that specifically antagonizes TLR2, IRS 954 is a nucleic acid molecule having the sequence shown in SEQ ID NO: 1 that specifically antagonizes TLR7 and TLR9, CPG 52364 is a small molecule that specifically antagonizes TLR7, TLR8, and TLR9, and IMO-3100 is a DNA-based antagonist of TLR7 and TLR9). In certain embodiments, a sample obtained from a subject comprises material such as, without limitation, amniotic fluid, blood, blood cells, cerebrospinal fluid, fine needle biopsy samples, peritoneal fluid, plasma, pleural fluid, saliva, semen, serum, sputum, tissue or tissue homogenates, tissue culture media, and/or urine. In certain embodiments, the sample comprises material obtained from a fluid or tissue associated with or affected by the inflammatory condition. For example, a sample from subject suffering from rheumatoid arthritis may be taken from the area affected by the rheumatoid arthritis, one or more TLRs that bind a ligand present in the sample may be identified, and a suitable treatment selected. Those skilled in the art will be aware of other TLRs that cause or mediate an immune condition, and will be able to employ methods described herein to determine whether a sample from a subject suffering from the immune condition contains ligands that bind those TLRs. Moreover, those skilled in the art will be aware of suitable therapeutic agents for antagonizing those TLRs. In certain embodiments, the solid supports, the cognate ligands, or both can be fluorescently labeled, and FRET can be used to detect displacement of the cognate ligands, as described more fully herein.

In certain embodiments, methods for assessing the presence or absence of a pathogen or a pathogen-derived toxin in a sample are provided. Such embodiments are useful, for example, when the sample comprises a pharmaceutical composition formulated for administration, e.g., parenteral administration, to a human subject. It is desirable that the sample be free of any agent that could cause an inflammatory or other adverse condition in a subject. Such an agent could be, for example, a bacterium (e.g., a gram negative or gram positive bacterium). Additionally or alternatively, such an agent could be a toxin secreted by a bacterium or that is otherwise present as a result of a live bacterium having previously been present in the pharmaceutical composition (e.g., as a result of a bacterium having lysed in the pharmaceutical formulation). Toxins can be any of the ligands recognized by TLRs, e.g., those that cause or mediate inflammatory conditions. Exemplary toxins include, without limitation, lipopolysaccharides, lipoproteins, flagellin, and nucleic acid molecules such as CpG.

In certain embodiments, methods for assessing the presence or absence of a pathogen or a pathogen-derived toxin in a sample comprise providing a plurality of biosensor complexes, each biosensor complex comprising a toll-like receptor (TLR) ligand binding domain conjugated to a solid support and bound to a cognate ligand, wherein at least one TLR ligand binding domain is different from the other TLR binding domains of the biosensor complexes. By contacting the plurality of biosensor complexes with a sample from the subject and detecting whether or not one or more of the cognate ligands are displaced (e.g., by detecting a decrease in binding between one or more TLRs and their cognate ligands on biosensor complexes), it is possible to determine whether the sample includes a pathogen or a pathogen-derived toxin. The plurality of biosensor complexes can include any of the variety of TLRs. If the presence of a pathogen or pathogen-derived toxin is detected (e.g., by detecting a decrease in binding between one or more TLRs and their cognate ligands on biosensor complexes), the sample can be deemed not suitable for administration, e.g., parenteral administration, to a subject. Alternatively, if the sample is determined not to be contaminated with a pathogen or pathogen-derived toxin, the sample can be deemed suitable for administration, e.g., parenteral administration, to a subject.

In certain embodiments, the present disclosure provides methods for detecting a ligand that binds a toll-like receptor comprising contacting a biosensor complex with a sample, which biosensor complex comprises a polypeptide conjugated to a solid support, wherein the polypeptide is bound by cognate ligand, and detecting a decrease in binding of the cognate ligand to the polypeptide. In certain embodiments, the polypeptide comprises a toll-like receptor ligand binding domain, and the cognate ligand binds the toll-like receptor ligand binding domain. In certain embodiments, the sample contains, or is suspected of containing, a test ligand that binds the toll-like receptor ligand binding domain. In certain embodiments, the solid support is fluorescently labeled.

In certain embodiments, the cognate ligand is fluorescently labeled, and the fluorescence emission spectrum of the fluorescently labeled solid support overlaps with the absorption spectrum of the fluorescently labeled cognate ligand. In certain embodiments, the test ligand displaces the fluorescently labeled cognate ligand from the biosensor complex, and detecting a decrease in binding of the cognate ligand to the polypeptide comprises detecting an increase in a first detectable emission from the fluorescently labeled solid support, detecting a decrease in a second detectable emission of the fluorescently labeled cognate ligand, or both.

In certain embodiments, the cognate ligand comprises a fluorescence quencher, and the fluorescence emission spectrum of the fluorescently labeled solid support overlaps with the absorption spectrum of the fluorescent quencher. In certain embodiments, the test ligand displaces the cognate ligand from the biosensor complex, and detecting a decrease in binding of the cognate ligand to the polypeptide comprises detecting an increase in a first detectable emission from the fluorescently labeled solid support.

In certain embodiments, the present disclosure provides methods for determining whether a test compound binds a polypeptide comprising contacting a biosensor complex with a sample, which biosensor complex comprises a polypeptide conjugated to a solid support, wherein the polypeptide is bound by cognate ligand, and detecting a decrease in binding of the cognate ligand to the polypeptide. In certain embodiments, the polypeptide comprises a toll-like receptor ligand binding domain, and the cognate ligand binds the toll-like receptor ligand binding domain. In certain embodiments, the solid support is fluorescently labeled.

In certain embodiments, the cognate ligand is fluorescently labeled, and the fluorescence emission spectrum of the fluorescently labeled solid support overlaps with the absorption spectrum of the fluorescently labeled cognate ligand. In certain embodiments, the test compound displaces the fluorescently labeled cognate ligand from the biosensor complex, and detecting a decrease in binding of the cognate ligand to the polypeptide comprises detecting an increase in a first detectable emission from the fluorescently labeled solid support, detecting a decrease in a second detectable emission of the fluorescently labeled cognate ligand, or both.

In certain embodiments, the cognate ligand comprises a fluorescence quencher, and the fluorescence emission spectrum of the fluorescently labeled solid support overlaps with the absorption spectrum of the fluorescent quencher. In certain embodiments, the test compound displaces the cognate ligand from the biosensor complex, and detecting a decrease in binding of the cognate ligand to the polypeptide comprises detecting an increase in a first detectable emission from the fluorescently labeled solid support.

In certain embodiments, the present disclosure provides methods of determining whether a test compound binds a polypeptide wherein a cognate ligand is not used. In certain embodiments, methods provided herein comprise providing a polypeptide conjugated to a solid support, wherein the polypeptide comprises a toll-like receptor ligand binding domain, contacting the polypeptide with the test compound, and detecting a binding of the test compound to the polypeptide. In certain embodiments, the solid support is fluorescently labeled. In certain embodiments, the test compound is fluorescently labeled, and the fluorescence emission spectrum of the fluorescently labeled solid support overlaps with the absorption spectrum of the fluorescently labeled test compound. In certain embodiments, detecting binding of the test compound to the polypeptide comprises detecting a decrease in a first detectable emission from the fluorescently labeled solid support.

In certain embodiments, the present disclosure provides methods for determining whether a test ligand binds a polypeptide comprising contacting a plurality of biosensor complexes with a sample, each biosensor complexes comprising a polypeptide conjugated to a solid support, wherein each polypeptide is bound by cognate ligand, and detecting a decrease in binding of at least one cognate ligand to at least one of the polypeptides. In certain embodiments, at least one polypeptide of the plurality comprises a toll-like receptor ligand binding domain. In certain embodiments, each polypeptide of the plurality comprises a toll-like receptor ligand binding domain. In certain embodiments, at least one toll-like receptor ligand binding domain of the plurality is different from at least one other toll-like receptor ligand binding domain of the plurality.

In certain embodiments, at least one solid support of a plurality of biosensor complexes, each of which comprises a solid support, is fluorescently labeled. In certain embodiments, at least one cognate ligand is fluorescently labeled, wherein the fluorescently labeled cognate ligand binds a polypeptide bound to a fluorescently labeled solid support. In certain embodiments, the fluorescence emission spectrum of the fluorescently labeled solid support overlaps with the absorption spectrum of the fluorescently labeled cognate ligand. In certain embodiments, the test ligand displaces a fluorescently labeled cognate ligand from a biosensor complex comprising a fluorescently labeled solid support. In certain embodiments, detecting a decrease in binding of the cognate ligand to the polypeptide comprises detecting an increase in a first detectable emission from the fluorescently labeled solid support, detecting a decrease in a second detectable emission of the fluorescently labeled cognate ligand, or both.

In certain embodiments, at least one cognate ligand of the plurality comprises a fluorescence quencher. In certain embodiments, the cognate ligand comprising a fluorescence quencher binds a polypeptide bound to the fluorescently labeled solid support. In certain embodiments, the fluorescence emission spectrum of the fluorescently labeled solid support overlaps with the absorption spectrum of the fluorescent quencher. In certain embodiments, the test ligand displaces a cognate ligand comprising a fluorescence quencher from a biosensor complex, and detecting a decrease in binding of the cognate ligand comprising the fluorescence quencher to the polypeptide comprises detecting an increase in a first detectable emission from the fluorescently labeled solid support.

In certain embodiments, the solid support comprises a quantum dot. In certain embodiments, the solid support comprises a gold nanoparticle. In certain embodiments, the polypeptide is covalently conjugated to the solid support. In certain embodiments, the polypeptide is noncovalently conjugated to the solid support.

In certain embodiments, a plurality of biosensor complexes can be used, each of which includes, e.g., a specific TLR or TLR ligand binding domain complexed to a labeled cognate ligand. Determining which biosensor complex or complexes have their cognate ligands displaced upon contact with a sample (e.g., by determining a difference in fluorescence from a fluorophore in the presence vs. the absence of a sample) will make it possible to reveal which TLR or TLRs interact with ligand(s) in the sample. As one non-limiting example, arrays containing the plurality of biosensor complexes can be used to determine which biosensor complex or complexes have their cognate ligands displaced upon contact with a sample. By determining which position(s) on the array exhibits a difference in fluorescence upon contact with the sample, and correlating this information with known positions of biosensor complexes comprising various TLRs or TLR ligand binding domains, it will be possible to determine which TLR or TLRs a test ligand in the sample binds. As another non-limiting example, biosensor complexes may exhibit characteristically different emission spectra upon having a fluorescently labeled cognate ligand displace. Thus, by determining the overall emission spectra of a plurality of biosensor complexes and comparing that with the overall emission spectra of the plurality upon contact with a sample containing a test ligand, it will be possible to determine which TLR or TLRs a test ligand in the sample binds. Those of ordinary skill in the art will be aware of other useful determination methods that can be used in accordance with the compositions and methods disclosed herein. This information can be used to determine a course of treatment for the subject. For example, a pharmaceutical or other compound known to affect the specific TLR or TLRs determined to interact with ligands in the sample can be administered to a subject, thus reducing or eliminating the disease or infection, and/or reducing the symptoms of the disease or infection.

In certain embodiments, compositions and methods disclosed herein can be used to determine whether a subject has one or more diseases and/or infections prior to exhibiting any symptoms. Such embodiments are useful, for example, in preventing the onset of symptoms and/or in preventing exacerbation of the disease or infection. For example, once it is determined that a subject has a disease or infection, a pharmaceutical or other compound can be administered to prevent onset of symptoms and/or in preventing exacerbation of the disease or infection.

In certain embodiments, compositions and methods disclosed herein can be used to determine whether a test compound binds a polypeptide. For example, a biosensor complex comprising a polypeptide conjugated to a solid support, and a cognate ligand that binds the polypeptide can be used to determine whether a test compound binds that polypeptide. In certain embodiments, a polypeptide of a biosensor complex comprises a TLR or TLR ligand binding domain. In certain embodiments, the solid support is detectably labeled, for example with a fluorescent label such as any of the exemplary fluorescent labels described herein. In certain embodiments, a cognate ligand is detectably labeled, for example with a fluorescent label such as any of the exemplary fluorescent labels described herein. Those of ordinary skill in the art will be aware of other suitable fluorescent labels.

In certain embodiments, compositions and methods used to determine whether a test compound binds a polypeptide comprise both a solid support and a cognate ligand that are detectably labeled, e.g. fluorescently labeled. In certain embodiments, fluorescent labels present on a solid support and a cognate ligand are chosen such that it is possible to determine whether the cognate ligand is part of a biosensor complex, e.g. by virtue of being bound to a TLR or TLR ligand binding domain. As is known to those of ordinary skill in the art, fluorophores exhibit characteristic electromagnetic absorption and emission spectra. In certain embodiments, fluorescent labels are chosen such that the emission spectrum of one overlaps with the absorption spectrum of another. For example, the emission spectrum of a fluorescent label present on a solid support can overlap with the absorption spectrum of a fluorescent label present on a cognate ligand. In such embodiments, excitation of the fluorescent label present on a solid support will result in excitation of the fluorescent label present on a cognate ligand. Thus, it is possible to determine whether a cognate ligand is present in a biosensor complex by measuring an increase in the emission spectrum of the cognate ligand fluorophore upon excitation of the solid support fluorophore. Additionally or alternatively, since at least a portion of the emission spectrum of the solid support fluorophore will be absorbed by the cognate ligand fluorophore, it is possible to determine whether a cognate ligand is present in a biosensor complex by measuring a decrease in the emission spectrum of the solid support fluorophore upon excitation.

In certain embodiments, a cognate ligand comprises a quencher, e.g., as quenchers described herein. Those of ordinary skill in the art will be aware of other quenchers that can be used in accordance with the compositions and methods disclosed herein. In certain embodiments, a fluorescent label present on a solid support and a quencher are chosen such that it is possible to determine whether the cognate ligand is part of a biosensor complex, e.g. by virtue of being bound to a TLR or TLR ligand binding domain. In certain embodiments, a fluorescent label on a solid support is chosen such that its emission spectrum overlaps with the absorption spectrum of a quencher on a cognate ligand. In such embodiments, it is possible to determine whether a cognate ligand is present in a biosensor complex by measuring a decrease in the emission spectrum of the solid support fluorophore upon excitation.

In certain embodiments, methods disclosed herein comprise contacting a biosensor complex with a test compound. As used herein, the term "test compound" refers to a compound that is tested to determine whether it binds to a polypeptide of the biosensor complex, e.g. a TLR or TLR ligand binding domain. In certain embodiments, binding by a test compound displaces a previously bound cognate ligand, and a decrease in binding of the cognate ligand is detected. Such displacement can be detected by use of suitable fluorescent labels and quenchers as described herein. For example, a fluorescently labeled cognate ligand will emit characteristic radiation upon excitation of a fluorescently labeled solid support when the emission and absorption spectra overlap. Upon displacement of the fluorescently labeled cognate ligand by the test compound, a difference in fluorescence can be detected. For example, upon such displacement, excitation of the fluorophore on the solid support will result in a decrease in the emission spectrum of the fluorescently labeled cognate ligand and a concomitant increase in the emission spectrum of the fluorescently labeled solid support (due to the fact that its emission radiation is not absorbed, or is absorbed to a lesser extent, by the cognate ligand fluorophore). As another example, a decrease in binding of a cognate ligand labeled with a quencher can be detected by detecting an increase in the fluorescence of a fluorescently labeled solid support upon displacement of the cognate ligand by the test compound.

In certain embodiments, compositions and methods disclosed herein can be used to determine whether a test compound binds a polypeptide without the use of a cognate ligand. For example, polypeptide conjugated to a solid support can be contacted with a test compound directly. In certain embodiments, such a conjugated polypeptide comprises a TLR ligand binding domain. In certain embodiments, such a conjugated polypeptide is not bound to a ligand prior to contacting it with the test compound. In certain embodiments, fluorescent labels present on a solid support and a test compound are chosen such that it is possible to determine whether the test compound has bound the polypeptide, e.g. by virtue of being bound to a TLR or TLR ligand binding domain. For example, the emission spectrum of a fluorescent label present on a solid support can overlap with the absorption spectrum of a fluorescent label present on a test compound. In such embodiments, excitation of the fluorescent label present on a solid support will result in excitation of the fluorescent label present on a test compound. Thus, it is possible to determine whether a test compound binds the polypeptide by measuring an increase in the emission spectrum of the test compound fluorophore upon excitation of the solid support fluorophore. Additionally or alternatively, since at least a portion of the emission spectrum of the solid support fluorophore will be absorbed by the test compound fluorophore, it is possible to determine whether a test compound binds the polypeptide by measuring a decrease in the emission spectrum of the solid support fluorophore upon excitation.

In certain embodiments, a test compound comprises a quencher, e.g., as quenchers described herein. Those of ordinary skill in the art will be aware of other quenchers that can be used in accordance with the compositions and methods disclosed herein. In certain embodiments, a fluorescent label present on a solid support and a quencher are chosen such that it is possible to determine whether the test compound binds the polypeptide, e.g. by virtue of being bound to a TLR or TLR ligand binding domain. In certain embodiments, a fluorescent label on a solid support is chosen such that its emission spectrum overlaps with the absorption spectrum of a quencher on a test compound. In such embodiments, it is possible to determine whether a test compound binds the polypeptide by measuring a decrease in the emission spectrum of the solid support fluorophore upon excitation.

In certain embodiments, the solid support is detectably labeled, for example with a fluorescent label such as any of the exemplary fluorescent labels described herein. In certain embodiments, the test compound is detectably labeled, for example with a fluorescent label such as any of the exemplary fluorescent labels described herein. Those of ordinary skill in the art will be aware of other suitable fluorescent labels. In certain embodiments, In certain embodiments, biosensor complexes can include pattern recognition molecules other than TLR polypeptides. For example, biosensor complexes can include NOD-like receptors (NLR) polypeptides in place of TLR polypeptides. Such NLR polypeptides can be conjugated to nanoparticles using techniques described above. Those of ordinary skill in the art will be aware of NLR and other polypeptides that can be used in the biosensor complexes and methods described herein, and will be able to use the compositions and methods disclosed herein in detecting binding of such polypeptides to ligands (e.g., ligands present in a sample).

In certain embodiments, methods are provided that utilize a toll-like receptor ligand binding domain bound by a cognate ligand, wherein the toll-like receptor ligand binding domain is not bound to a solid support. In certain embodiments, the toll-like receptor ligand binding domain, the cognate ligand, or both are fluorescently labeled, and FRET is used to determine whether the toll-like receptor ligand binding domain is bound by the cognate ligand. For example, a toll-like receptor ligand binding domain bound by a cognate ligand, each of which is fluorescently labeled for use in FRET, is contacted with a sample, and binding of the toll-like receptor ligand binding domain bound to the cognate ligand is determined. If contact with the sample, results in displacement (e.g., as determined by a decrease in binding between the toll-like receptor ligand binding domain and its cognate ligand), it can be determined that the sample comprises an agent that either disrupts binding or contains a TLR ligand. Those skilled in the art will be able to employ toll-like receptor ligand binding domains bound by their cognate ligands, in which the toll-like receptor ligand binding domains are not bound to a solid support, in accordance with other compositions and methods disclosed herein.

The invention is further illustrated by the following examples. The examples are provided for illustrative purposes only. They are not to be construed as limiting the scope or content of the invention in any way.

EXAMPLES

Example 1

The following materials and methods were used in the Examples disclosed herein.

Construction of a TLR Construct:

The cloning of the FRET constructs involved to separate cloning steps. First the CDS for YFP was amplified by PCR from a plasmid containing the coding sequence for YFP fused to the signal for geranylgeranylation from the COOH-terminal CLLL from Rho (pYFP-GerGer) using primers 5'-CTGAACGAATTCGCCGCTAGCATGGTGAGCAAGGGC-3' (SEQ ID NO:3) and 5'-GGATATCTAGACTCGAGTTACTTGTACAGCTCGTCC-3' (SEQ ID NO:4). The PCR reaction was digested with EcoRI and XbaI. The cut product was gel purified and ligated into EcoRI and XbaI cut pCDNA3 (Invitrogen). In the second cloning step CFP was amplified by PCR from a vector containing the CFP CDS linked to an NH2-terminal sequence encoding for a myristoylation and palmitoylation site using the following primers: 5'-GACCCGGATCCGCGGCCGCCACCATGGGCTGC-3' (SEQ ID NO:5) and 5'-GATGGGAATTCGGCATCGATTGCCTTGTACAGCTCGTCCA-3' (SEQ ID NO:6). The PCR product was digested with BamHI and EcoR I and ligated into BamHI and EcoRI cut vector obtained from the first cloning step. The final vector yields a CFP-YFP chimeric protein (5'CFP, 3' YFP'). There is an 18 basepair spacer between CFP and YFP, which encode the following 9 amino acids: AIDAEFAAS. The plasmid is based in pCDNA3.

Stable Cell Lines:

Human embryonic kidney cells (HEK) were stably transfected according to the following procedure. HEK cells were grown in DMEM (Biowhittaker), 10% FBS (Hyclone) and 10 ug/ml Ciprofloxacin (Cellgro). Cells were transfected using calcium phosphate transfection with plasmids encoding CFP, YFP or a fusion protein of CFP and YFP (CFP-YFP, FRET-construct). After 24 h the cell culture medium was supplemented with 1 mg/ml G418 sulfate (Cellgro). 14 days after transfection, cells were positively sorted for high expressors (CFP, YFP, or FRET) using a Becton Dickinson Vantage cell sorter. Clonal cell lines were established by limiting dilution.

EMSA (Gel-Shift Assay):

Gel-shift assays were performed in regular electrophoresis basins. The gels were run in 1×TRIS-glycine buffer pH 8.0 (diluted from 10× solution containing 0.25 mM TRIS base and 1.92 M glycine, Fisher Scientific) at 100 V constant voltage, and the gels contained 1.5% agarose and were cast in the same buffer. The samples for gel-shift assays were mixed together in 1×TRIS-glycine buffer. The numerical values in the tables in FIGS. 4-8 for gel-shift assays show pmols of material in the volume of 15 µl (for 2 or 3 components) or 20 µl (for 4 components). The samples were loaded into the wells after supplemented with 5 µl 50:50 glycerol:TRIS-glycine.

Proteins:

The protein mRAGE is the mouse-specific receptor for advanced glycation endproducts that binds several ligands (non-enzymatically altered proteins, DNA, etc.) associated with aging, diabetes and inflammation. Two synthetic peptides that were engineered with the 6×His-tag on C-terminal end, and a lysine (K) on the N-terminal end were used for fluorescent dye conjugation, and two different length polyproline (PX) sequences in between: NH2-KP5H6-COOH and NH2-KP15H6-COOH (custom produced by Invitrogen). The peptides were labeled with AlexaFluor647-succinimidyl ester (Invitrogen), and the labeled end-product was purified with HPLC.

Nanomaterials:

The gold nanoparticles were approx. 2.1 nm large, and functionalized with two $HS-(CH_2)_{11}-O-(CH_2CH_2-O)_4-CH_2-CO-NH-(CH_2)_5-NTA-Ni_2+$ per particle on average. The concentration was 35 µM. QDot550 is a CdSe-core quantum dot, with ZnS protective shell and DHLA surface-coating. The concentration was ~8 µM, and the fluorescence emission maximum was about 552 nm. QDot605 is a CdSe-core quantum dot, with ZnS protective shell and PEG (1100) surface-coating. The concentration was ~10 µM, and the fluorescence emission maximum was about 605 nm.

Example 2

To verify the binding capabilities of quantum dots and functionalized gold particles to 6×His-tagged proteins, Electrophoretic Mobility Shift Assays (EMSA) were performed. EMSA can reveal whether two components of a mixture are bound to each other, as the bound product has higher mass and different charge, so it will travel less distance in the gel given the same electric field. Such a "hindrance of mobility", or shift can be seen in FIG. 4, where QDot550 was mixed together with increasing amount of protein.

Example 3

Figure 5:
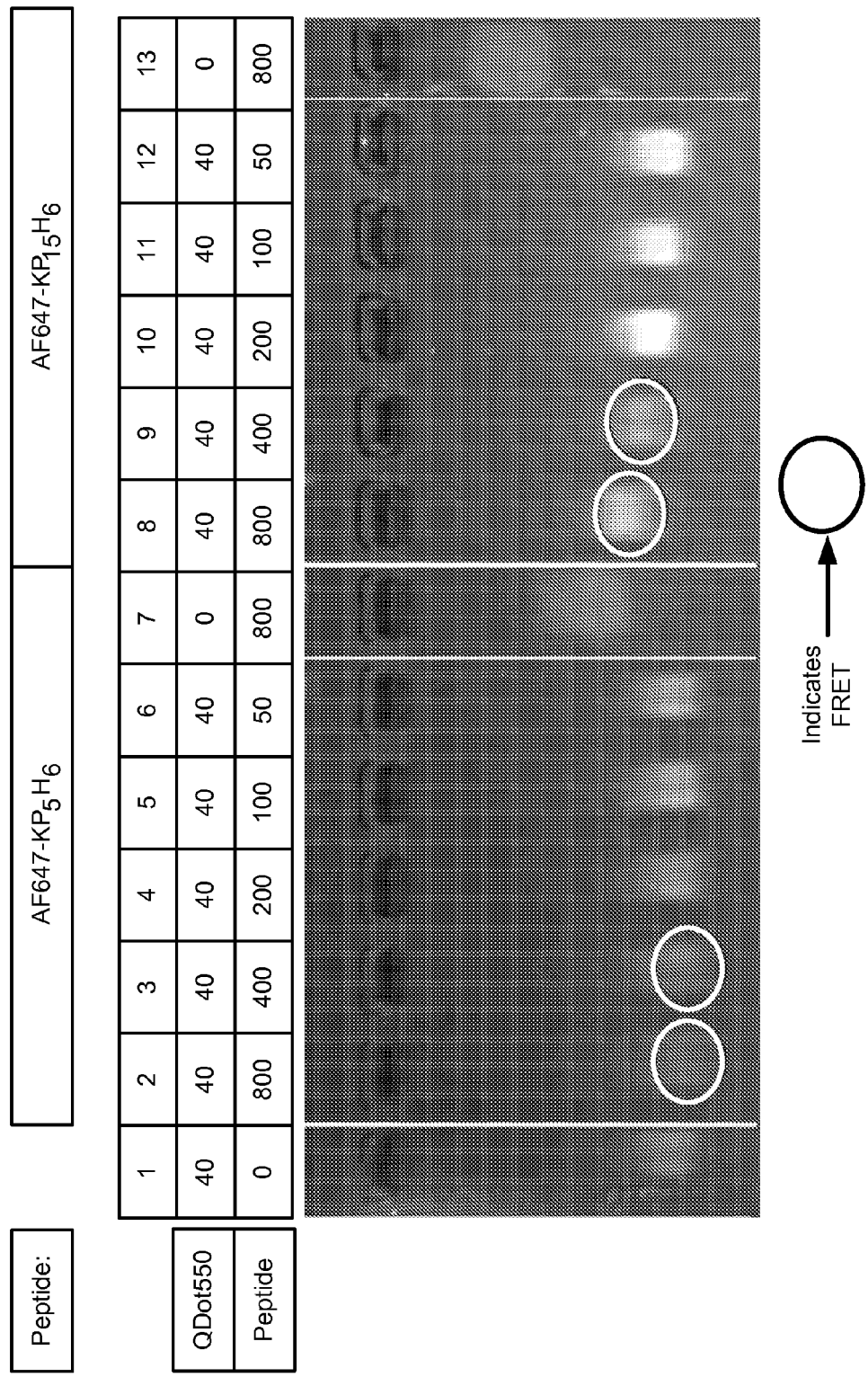
FIG. 5 is a photograph of an agarose gel showing binding of AlexaFluor647-labeled 6×His-containing small peptides to QDot550-DHLA in increasing ratio. Red and green colors (observed in the color photograph) show the fluorescence of AlexaFluor647 and QDot550, respectively. Blue circles indicate the loss of QDot550 fluorescence due to FRET to AlexaFluor647.

Two synthetic peptides ($KP_5H_6$ and $KP_{15}H_6$) labeled with AlexaFluor 647 were bound to quantum dots in increasing ratios. As can be seen in FIG. 5, the fluorescence signal of the quantum dot decreased due the presence of the synthetic peptides. The decrease was even more pronounced with the peptide containing the shorter poly-proline linker, as FRET efficiency increases with decreasing distance. Thus, a long-wavelength fluorophore can effectively quench the fluorescence of quantum dots via FRET.

Figure 6:
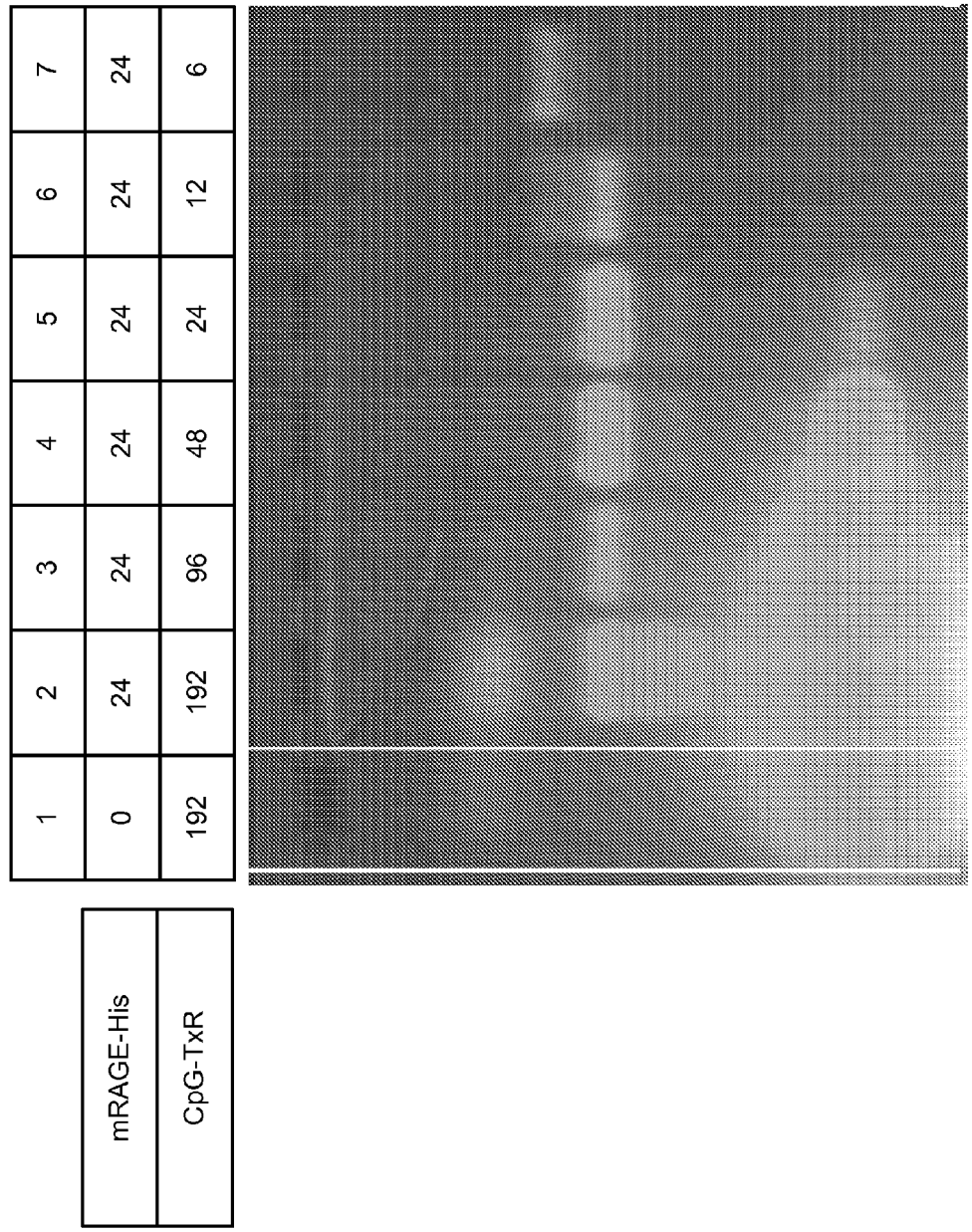
FIG. 6 is a photograph of an agarose gel showing binding of TexasRed-labeled CpG to mRAGE-His in increasing ratio. Red color (observed in the color photograph) represents the fluorescence emission of TexasRed.
Figure 7:
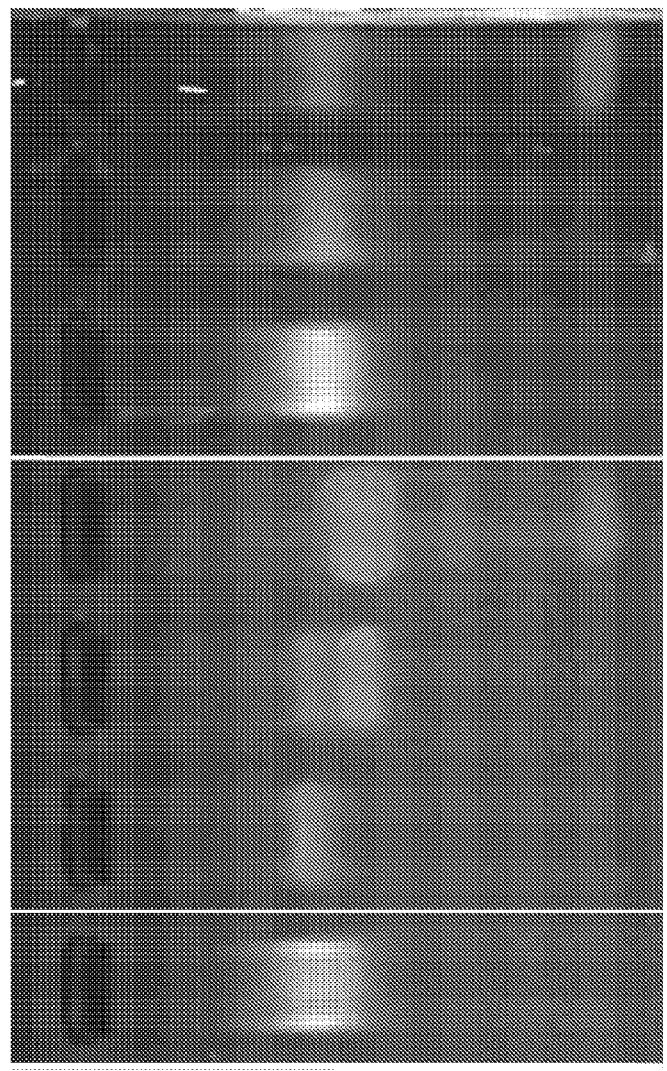
FIG. 7 is a photograph of an agarose gel showing binding of mRAGE-His to Cy5-labeled CpG and QDot605-PEG(1100). Red and green colors (observed in the color photograph) represent the fluorescence of Cy5 and QDot605, respectively. The top bands in lanes 5-7 show co-fluorescence of Cy5-labeled CpG and QDot605-PEG.

The binding of fluorescent ligands (CpG, a short DNA sequence, which is recognized by TLR9 and other DNA-sensing proteins) to the proteins was also verified with increasing ligand-to-protein ratio in FIG. 6.

Example 4

In a functional immuno-biosensor, a nanoparticle, at least one pattern sensing protein and its fluorescently labeled ligand should be present in the same complex. Evidence for such assembled complexes can be seen in FIG. 7 (Lanes 5-7) for quantum dots.

Figure 8:
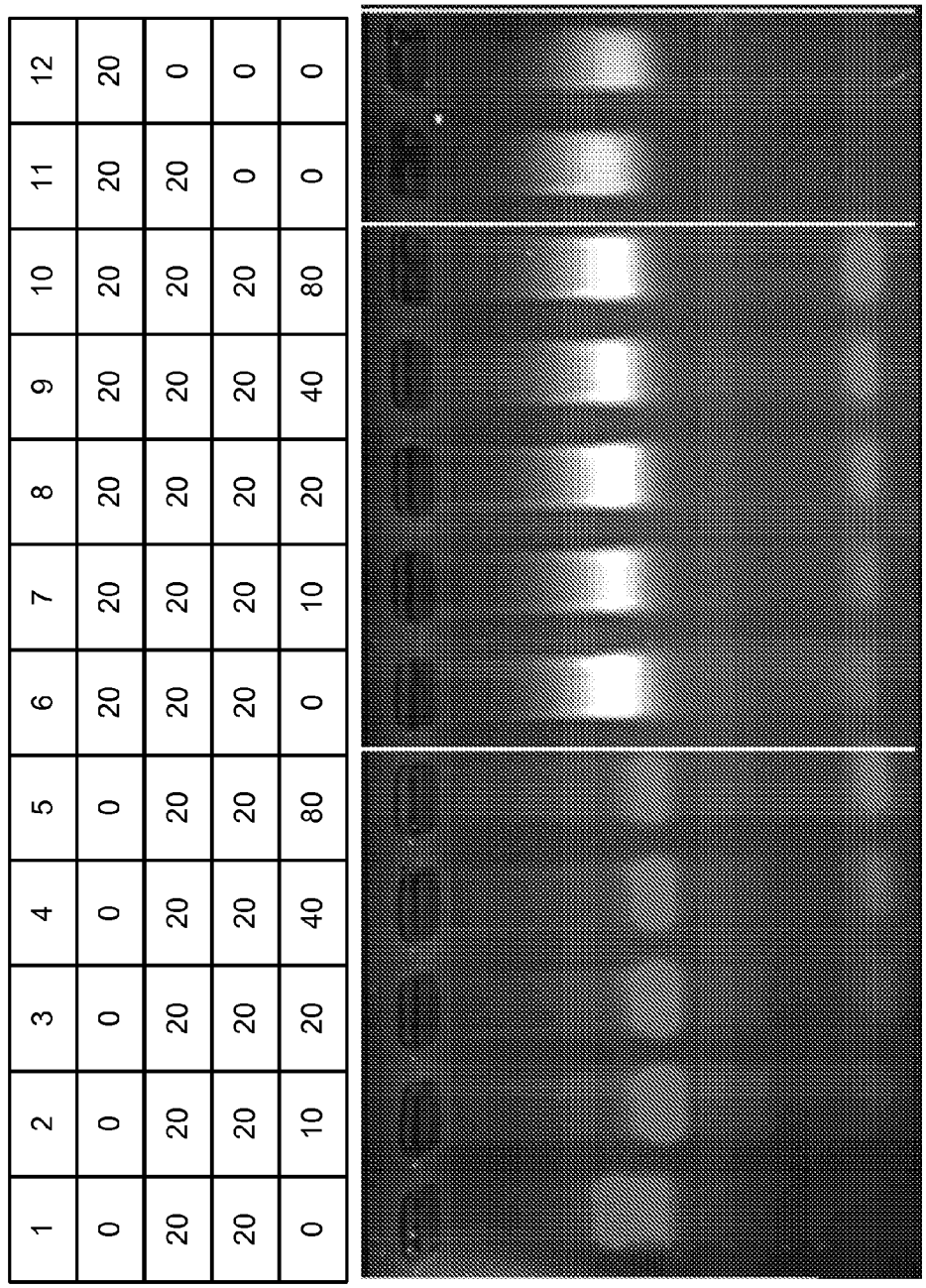
FIG. 8 is a photograph of an agarose gel showing competition of CpG (2007) with Cy5-labeled CpG on mRAGE-His alone, or when bound to QDot605-PEG(1100). Red and green colors (observed in the color photograph) represent the fluorescence of Cy5 (lanes 1-5) and QDot605 (lanes 11-12), respectively. The top bands in lanes 6-10 show co-fluorescence of Cy5-labeled CpG on mRAGE-His.

One advantageous aspect of a functional biosensor is that the fluorescently labeled ligand can be displaced from the biosensor with natural ligands, e.g., those that can occur in physiological or pathological subject sera. FIG. 8 shows that an unlabeled CpG can compete with its labeled counterpart in binding to its receptor as it is or when the receptor is bound to a quantum dot. Thus, this Example shows that a fluorescently labeled ligand can be displaced from the biosensor with natural ligands.

Example 5

Figure 10A:
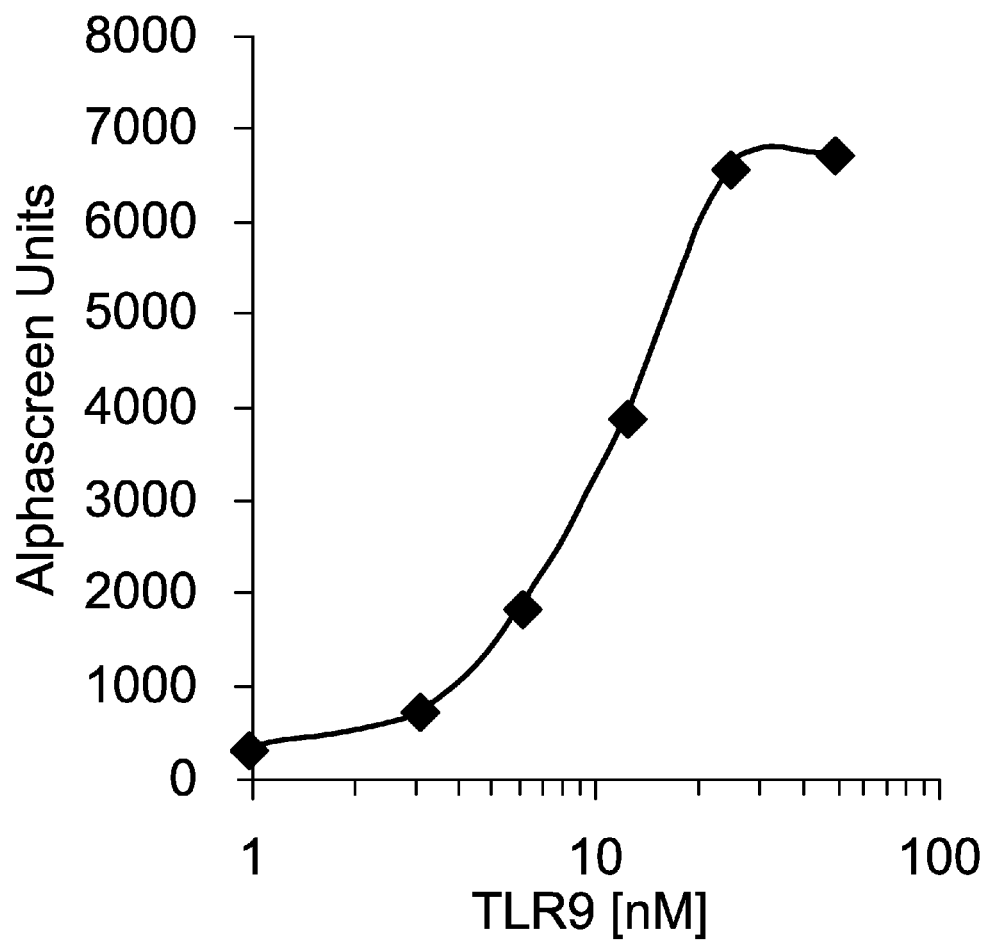
FIG. 10A is a line graph showing purified TLR9 ectodomain protein binds to CpG-DNA in a dose-dependent manner. FLAG-TLR9-ECD-6HIS was purified and binding to biotinylated DNA was assessed by AlphaScreen assay (manufactured by PerkinElmer). TLR9 and biotinylated DNA were incubated in buffer for 30 minutes at 24 degrees C. Subsequently, nickel-coated acceptor beads and streptavidin-coated donor beads were added for a further 30 min at 24 degrees C. in 12.5 µl final volume in wells of 384 well plates.
Figure 10B:
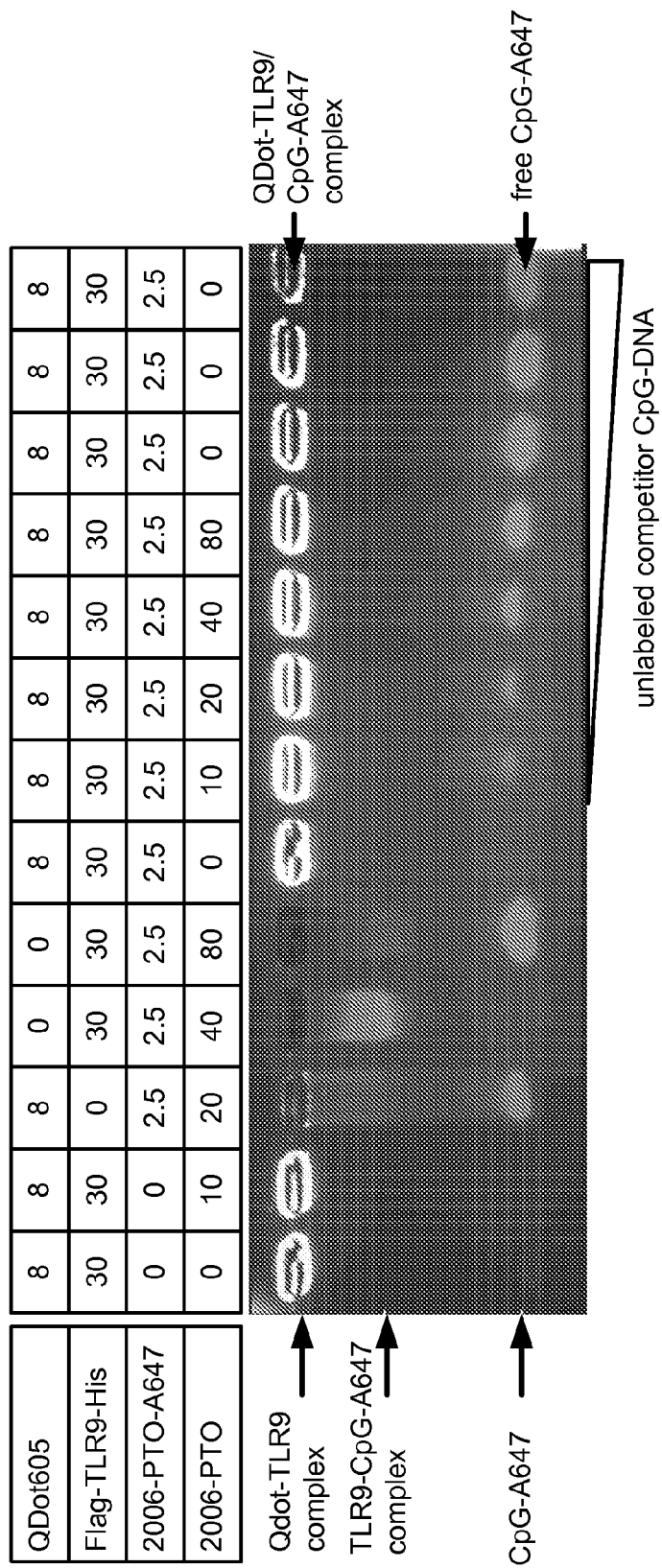
FIG. 10B is a photograph of an agarose gel showing that unlabeled CpG DNA competes with and displaces labeled CpG bound to FLAG-TLR9-ECD-6HIS. Pegylated QDot605 were mixed with recombinant purified TLR9 alone or together with Alexa647-tagged CpG DNA alone or together with increasing concentrations of unlabeled competitor DNA. Mixtures were electrophoresed in a 1% agarose gel and the gel was imaged for the QDot (shown in green, observed in the color photograph) and CpG-DNA fluorescence (shown in red, observed in the color photograph) and the images were overlaid electronically. Co-fluorescence was observed as yellow (observed in the color photograph). The top bands in lanes 6-13 show decreasing amounts of co-fluorescence, and increasing relative amounts of Qdot fluorescence, while the bottom bands in lanes 6-13 show increasing amounts of displaced labeled CpG-DNA.

The TLR9 ectodomain carrying a FLAG-tag at the N-terminus and a 6-His tag at the C-terminus was engineered. This protein was expressed in mammalian HEK cells, purified via by affinity purification using the FLAG and His tags, and tested for the ability to bind CpG-DNA. As shown in FIG. 10A, the purified TLR9 ectodomain protein bound to CpG-DNA in a dose-dependent manner, as assessed by Alphascreen technology. Next, the TLR9 ectodomain protein was incubated with fluorescent QDot605 and the ability of the protein to bind to the Qdot was analyzed. As seen in FIG. 10B, TLR9-bound QDots remained in the well of the agarose gel, indicating that the protein/QDot complex is too large enter this gel (lanes 1 and 2). This inability to enter the gel did not occur because the TLR9 protein was aggregated; TLR9/fluorescent DNA complexes (lane 4) migrated efficiently into the gel. The addition of fluorescent DNA to the QDot/TLR9 complex led to a shift of the fluorescent DNA to the complex (lane 6) indicating that the complex of QDot and TLR9 can effectively bind to the fluorescent ligand. Furthermore, addition of fluorescent DNA to the QDot/TLR9 complex led to a change of color of the bead from green to yellow (visible in a color photograph of the gel), indicative of FRET. Addition of increasing amounts of unlabeled competitor DNA led to a dose-responsive release of the fluorescent DNA from the QDot/TLR9 complex, due to competition between the labeled and unlabeled DNA (lanes labeled "unlabeled competitor CpG-NDA").

Example 6

Figure 11A:
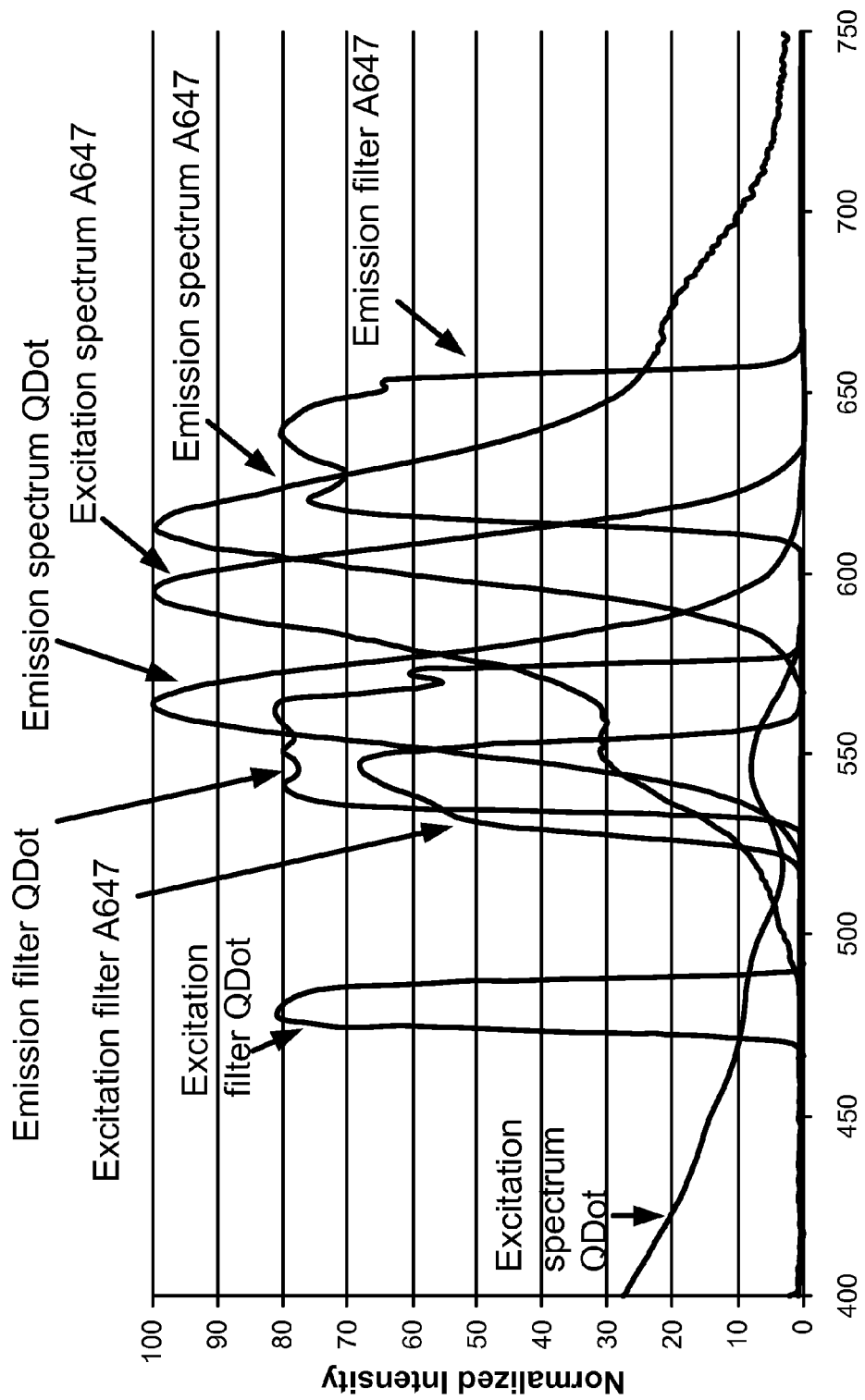
FIGS. 11A-C show sensitized emission FRET determination of QDot605/TLR9 nanosensor.
Figures 11B, 11C:
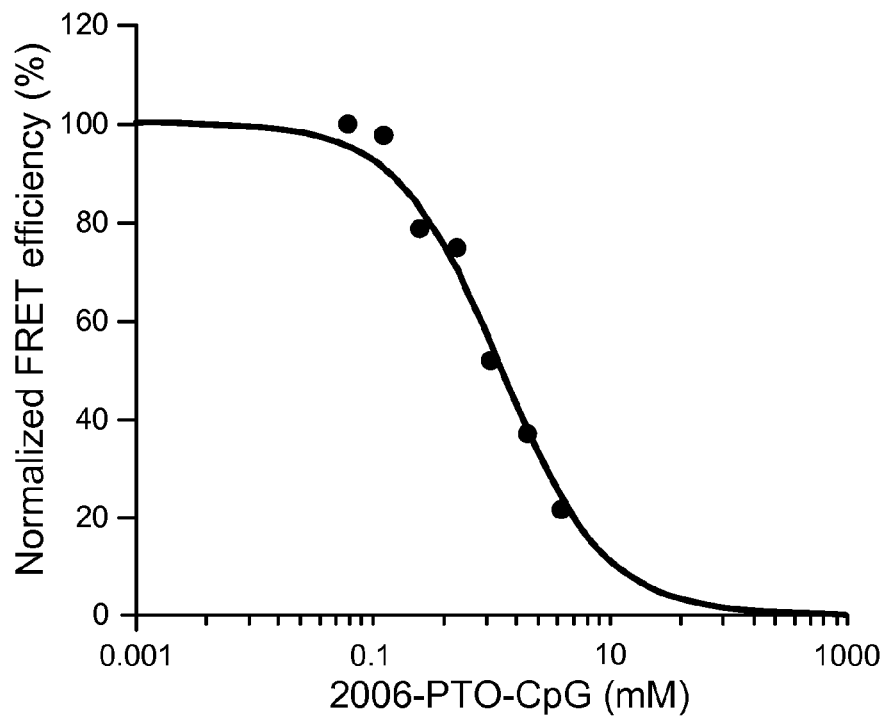

A plate-based fluorescence FRET assay to quantitatively determine the amount of FRET between the QDot and the fluorescent DNA bound to TLR9 was developed. FIG. 11A shows the fluorescence filter set-up (excitation and emission filters) together with the excitation and emission spectra of the QDot and the fluorescent DNA used for these studies. With any intensity-based FRET assessment, fluorescence crossexcitation and bleed-through can be a technical hurdle. In particular, depending on the selected FRET fluorophore pair, the fluorescence bleed-through of donor fluorescence into the FRET channel (excitation of donor; emission of acceptor) can be substantial. In order to account for the fluorescence cross-excitation and bleed-through factors, mathematical algorithms for the calculation of the corrected sensitized emission FRET were utilized. The mathematical algorithms that were utilized are shown in FIG. 11B and were adapted from the calculations necessary to analyze FRET by flow cytometry. The plates were then measured using a fluorescence plate reader (Perkin Elmer, Envision) and the corrected sensitized emission FRET valued were calculated. FIG. 11C demonstrates an example of normalized FRET measurements of FRET between QDot and TLR9/fluorescent CpG-DNA performed in 384-well plates. Addition of increasing amounts of unlabeled competitor DNA led to a dose-responsive loss of FRET, indicating functionality of the TLR9-based DNA nanosensor.

Since the TLR9/DNA interaction is mostly dependent on charge/charge interactions, the pH of the buffer and the ion concentration can influence the sensitivity and specificity of the molecular interaction. The miniaturization of this TLR-based ligand binding assay, as demonstrated in this Example, allows optimization of signal to noise ratios, specificity and sensitivity of the sensors since the small reaction volume does not require large amounts of protein or ligand. Moreover, this Example demonstrates that it is possible to optimize the stability and purification of nanosensors based on multiple pattern recognition molecules.

What is claimed is:

1. A method for selecting a treatment for a subject having an inflammatory condition, the method comprising:
providing a plurality of biosensor complexes, each biosensor complex comprising a toll-like receptor (TLR) extracellular domain conjugated to a water-solubilized quantum dot, wherein at least one TLR extracellular domain is different from the other TLR extracellular domains of the biosensor complexes and at least one TLR extracellular domain is a TLR4 extracellular domain, wherein each biosensor complex further comprises a cognate ligand bound to the TLR extracellular domain, and wherein at least one cognate ligand is fluorescently labeled;
providing a sample comprising a biological fluid or tissue from the subject;
contacting the sample to the plurality of biosensor complexes;
detecting a change in fluorescence to detect a change in binding of at least one cognate ligand to its TLR extracellular domain, wherein a change in binding indicates the presence of a ligand for the TLR extracellular domain in the sample;
identifying which biosensor complex or complexes bind ligands present in the sample; and
selecting a treatment for the subject based on the identity of the TLR extracellular domain bound by the ligand in the sample.

2. The method of claim 1, wherein:
the fluorescence emission spectrum of the quantum dot overlaps with the absorption spectrum of the fluorescently labeled cognate ligand, and a decrease in binding is detected by detecting a change in fluorescence emissions from the biosensor complex.

3. The method of claim 1, wherein the treatment comprises administration of a therapeutic agent to the subject, wherein the therapeutic agent specifically inhibits the TLR extracellular domain bound by the ligand in the sample.

4. The method of claim 3, wherein at least one of the TLR extracellular domains bound by the ligand in the sample is a TLR4 extracellular domain, and wherein the therapeutic agent comprises TAK-242.

5. The method of claim 3, wherein at least one of the TLR extracellular domains bound by the ligand in the sample is a TLR4 extracellular domain, and wherein the therapeutic agent comprises eritoran.

6. The method of claim 3, wherein at least one of the TLR extracellular domains bound by the ligand in the sample is a TLR2 extracellular domain, and wherein the therapeutic agent comprises the humanized antibody OPN-305.

7. The method of claim 3, wherein at least one of the extracellular domains bound by the ligand in the sample is a TLR7 or TLR9 extracellular domain, and wherein the therapeutic agent comprises a nucleic acid molecule shown in SEQ ID NO: 1.

8. The method of claim 3, wherein at least one of the TLR extracellular domains bound by the ligand in the sample is a TLR7 or TLR9 extracellular domain, and wherein the therapeutic agent comprises IMO-3100.

9. The method of claim 3, wherein at least one of the TLR extracellular domains bound by the ligand in the sample is a TLR7, TLR8, or TLR9 extracellular domain, and wherein the therapeutic agent comprises CPG 52364.

10. The method of claim 1, wherein the subject is a human.

11. The method of claim 1, wherein the sample comprises a material obtained from a subject, the material selected from the group consisting of: amniotic fluid, blood, blood cells, cerebrospinal fluid, fine needle biopsy samples, peritoneal fluid, plasma, pleural fluid, saliva, semen, serum, sputum, tissue or tissue homogenates, tissue culture media, and urine.

12. The method of claim 11, wherein the sample comprises material obtained from a fluid or tissue associated with or affected by the inflammatory condition.

13. The method of claim 1, wherein the plurality of biosensor complexes are present on an array comprising a plurality of individually addressable areas, wherein each addressable area includes complexes having the same TLR extracellular domain, and at least two of the individually addressable areas include complexes having different TLR extracellular domains.

14. The method of claim 1, wherein at least one of the TLR extracellular domains is selected from the group consisting of TLR2, TLR7, TLR8, and TLR9 extracellular domains.

15. The method of claim 1, wherein the plurality of biosensor complexes comprises biosensor complexes comprising each of TLR2, TLR4, TLR7, TLR8, and TLR9 extracellular domains.

16. The method of claim 3, wherein the therapeutic agent comprises TAK-242, eritoran, a humanized antibody OPN-305, a nucleic acid molecule comprising the nucleic acid sequence of SEQ ID NO:1, IMO-3100, or CPG 52364.

17. The method of claim 1, wherein the quantum dot is conjugated to dihydrolipoic acid.

18. The method of claim 1, wherein the quantum dot is coated with polyethylene glycol.

* * * * *